(12) United States Patent
Jung et al.

(10) Patent No.: US 10,111,623 B2
(45) Date of Patent: Oct. 30, 2018

(54) MULTI-ELECTRODE MAPPING CATHETER

(71) Applicant: X-RHYTHM, LLC, Beachwood, OH (US)

(72) Inventors: Eugene Jung, Beachwood, OH (US); Robert S. Jung, Fremont, CA (US)

(73) Assignee: X-RHYTHM, LLC, Beachwood, OH (US)

( * ) Notice: Subject to any disclaimer, the term of this patent is extended or adjusted under 35 U.S.C. 154(b) by 499 days.

(21) Appl. No.: 14/711,308

(22) Filed: May 13, 2015

(65) Prior Publication Data

US 2016/0073960 A1 Mar. 17, 2016

Related U.S. Application Data

(60) Provisional application No. 62/050,071, filed on Sep. 12, 2014.

(51) Int. Cl.
| | |
|---|---|
| *A61B 5/00* | (2006.01) |
| *A61M 25/00* | (2006.01) |
| *A61M 25/06* | (2006.01) |
| *A61B 5/042* | (2006.01) |

(Continued)

(52) U.S. Cl.
CPC .......... *A61B 5/6858* (2013.01); *A61B 5/0422* (2013.01); *A61B 18/1492* (2013.01); *A61B 2018/00357* (2013.01); *A61B 2018/00577* (2013.01); *A61B 2018/00642* (2013.01); *A61B 2018/00839* (2013.01)

(58) Field of Classification Search
None
See application file for complete search history.

(56) References Cited

U.S. PATENT DOCUMENTS

| | | |
|---|---|---|
| 4,699,147 A | 10/1987 | Chilson et al. |
| 5,309,910 A | 5/1994 | Edwards et al. |
| 5,415,166 A | 5/1995 | Imran |

(Continued)

OTHER PUBLICATIONS

Intl. Search Report and Written Opinion from PCT/US2015/030622, dated Jul. 27, 2015, 3 pages.

(Continued)

*Primary Examiner* — Brian T Gedeon
(74) *Attorney, Agent, or Firm* — Thomas A. Runk; Brooks Kushman P.C.

(57) ABSTRACT

A multi-electrode mapping catheter for endocardial contact mapping of a heart chamber includes an expandable basket movable between a contracted configuration and a pre-shaped deployed configuration, the expandable basket including a plurality of flexible splines. Each spline includes a flex circuit and an electrode for mapping. A catheter shaft extending from the basket includes a lumen formed therethrough for receiving an ablation catheter for placement within the expandable basket. Each flex circuit includes a conductor that directly connects the proximal end of the catheter shaft to an electrode as a single continuous piece. In another embodiment, a shaft flex circuit extends along the length of the shaft and is electrically connected to a basket flex circuit. The expandable basket maintains the electrodes in direct contact with the wall of the heart while accommodating wall motion of the beating heart during mapping and can continually map while ablating.

18 Claims, 14 Drawing Sheets

(51) Int. Cl.
*A61B 18/14* (2006.01)
*A61B 18/00* (2006.01)

(56) References Cited

U.S. PATENT DOCUMENTS

| | | | |
|---|---|---|---|
| 5,425,364 A | 6/1995 | Imran | |
| 5,549,108 A | 8/1996 | Edwards et al. | |
| 5,782,239 A | 7/1998 | Webster et al. | |
| 5,782,899 A * | 7/1998 | Imran | A61B 18/1492 |
| | | | 600/374 |
| 5,911,739 A | 6/1999 | Kordis et al. | |
| 5,964,753 A | 10/1999 | Edwards | |
| 6,014,579 A * | 1/2000 | Pomeranz | A61B 5/0422 |
| | | | 600/374 |
| 6,163,716 A | 12/2000 | Edwards et al. | |
| 6,216,043 B1 | 4/2001 | Swanson et al. | |
| 6,592,520 B1 * | 7/2003 | Peszynski | A61B 8/12 |
| | | | 600/437 |
| 6,712,767 B2 * | 3/2004 | Hossack | A61B 8/12 |
| | | | 600/467 |
| 6,771,996 B2 | 8/2004 | Bowe et al. | |
| 6,926,669 B1 | 8/2005 | Stewart et al. | |
| 7,742,795 B2 | 6/2010 | Stone et al. | |
| 8,097,926 B2 | 1/2012 | De Graff et al. | |
| 8,103,327 B2 | 1/2012 | Harlev et al. | |
| 8,180,460 B2 | 5/2012 | Nevsmith et al. | |
| 8,364,234 B2 | 1/2013 | Kordis et al. | |
| 8,504,133 B2 | 8/2013 | Kordis et al. | |
| 8,560,086 B2 * | 10/2013 | Just | A61B 5/0422 |
| | | | 600/374 |
| 8,755,861 B2 | 6/2014 | Harlev et al. | |
| 9,060,756 B2 * | 6/2015 | Bencini | A61B 18/02 |
| 9,314,618 B2 * | 4/2016 | Imran | A61N 1/0553 |
| 9,522,035 B2 * | 12/2016 | Highsmith | A61B 18/1492 |
| 9,560,982 B2 * | 2/2017 | Kordis | A61B 5/0422 |
| 9,894,756 B2 * | 2/2018 | Weinkam | H05K 1/028 |
| 2001/0029371 A1 | 10/2001 | Kordis | |
| 2005/0033136 A1 | 2/2005 | Govari et al. | |
| 2009/0171274 A1 | 7/2009 | Harlev et al. | |
| 2009/0240249 A1 * | 9/2009 | Chan | A61B 18/1492 |
| | | | 606/41 |
| 2012/0143298 A1 * | 6/2012 | Just | A61B 5/0422 |
| | | | 607/122 |
| 2013/0066220 A1 | 3/2013 | Weinkam et al. | |
| 2013/0172715 A1 | 7/2013 | Just et al. | |
| 2014/0336636 A1 * | 11/2014 | Huszar | A61B 1/00082 |
| | | | 606/41 |
| 2015/0196354 A1 * | 7/2015 | Haverkost | A61B 18/1492 |
| | | | 606/41 |

OTHER PUBLICATIONS

Extended European Search Report from EP Appl. No. 15840100.0 (PCT/US2015/030622), dated Jul. 13, 2018, 4 pages.

* cited by examiner

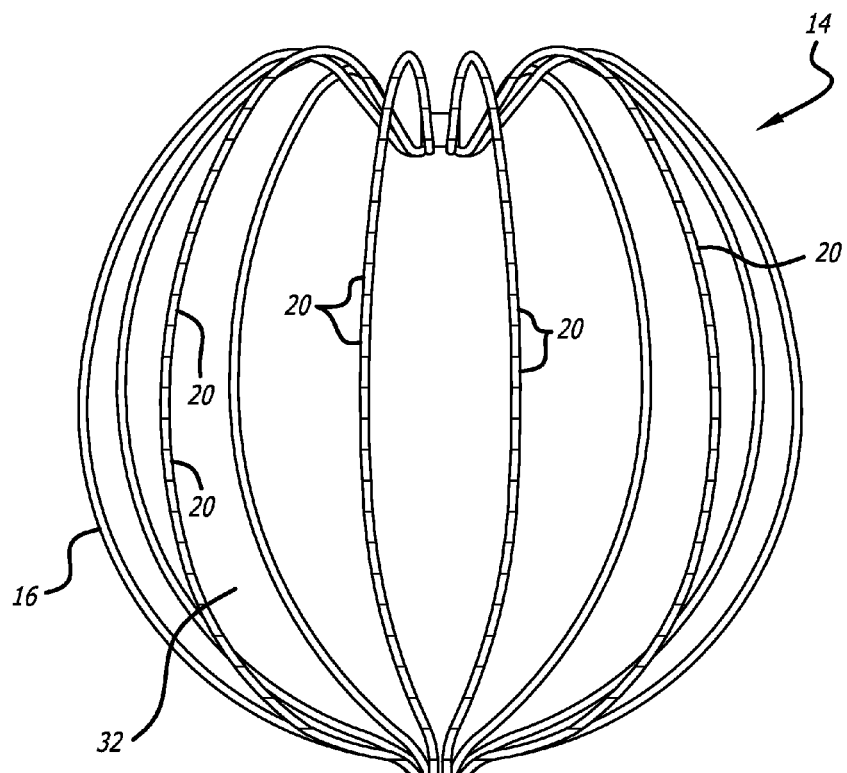
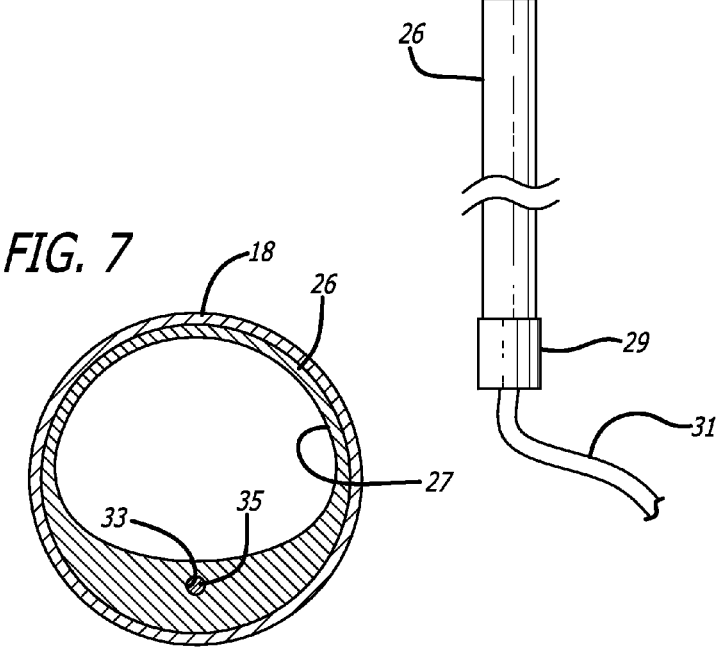
FIG. 6
FIG. 7

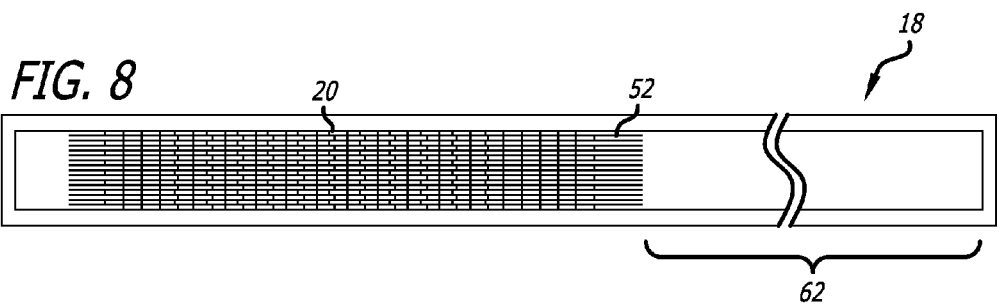
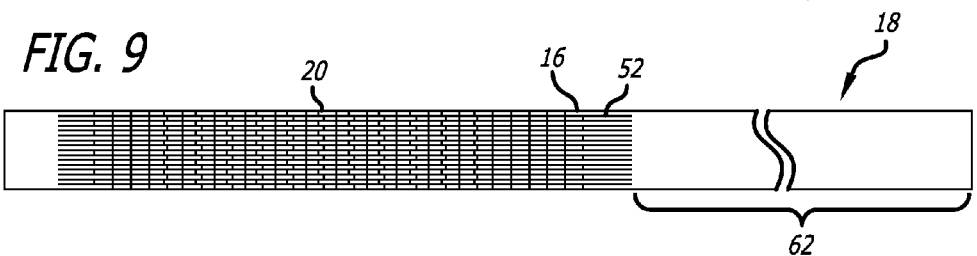
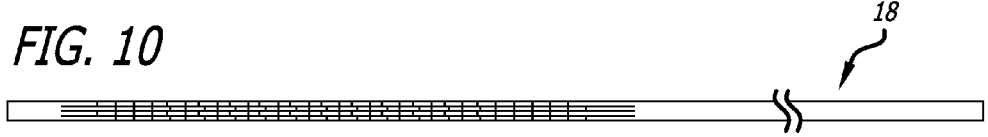
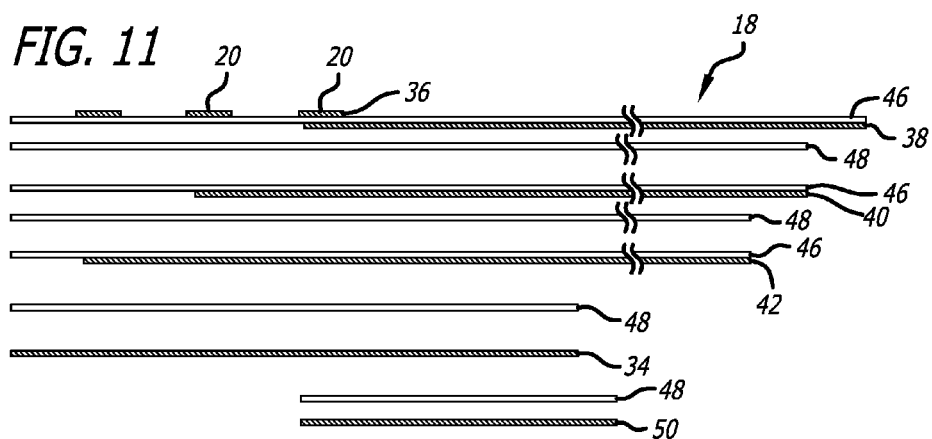
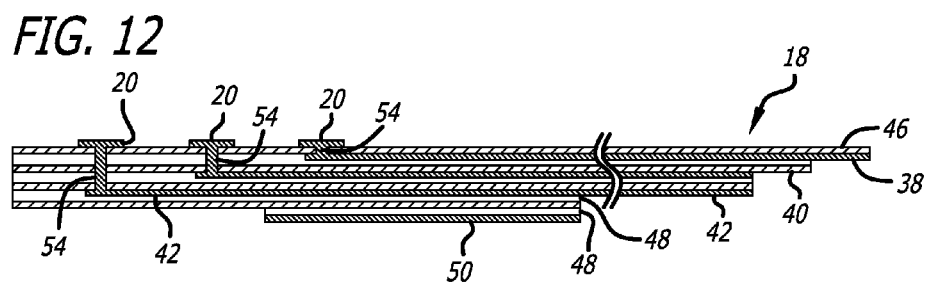

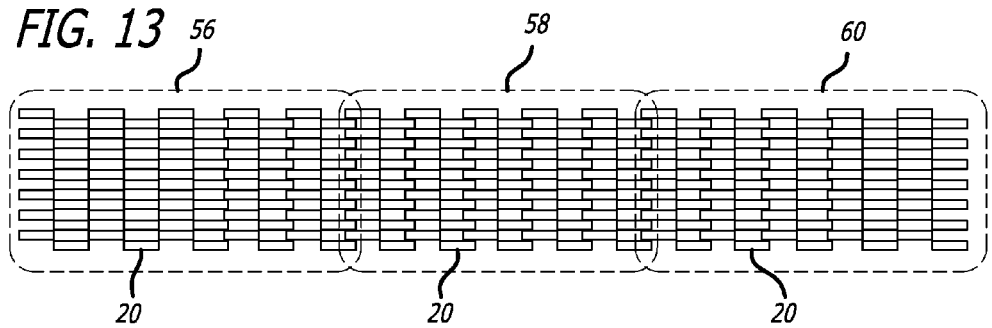
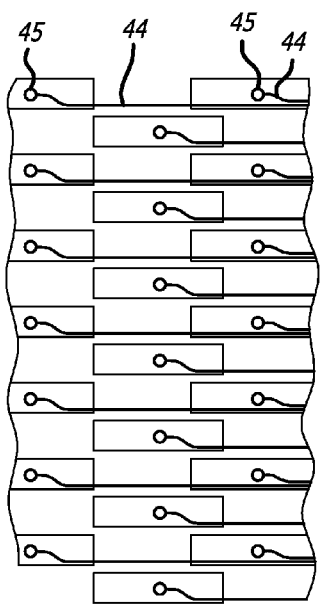 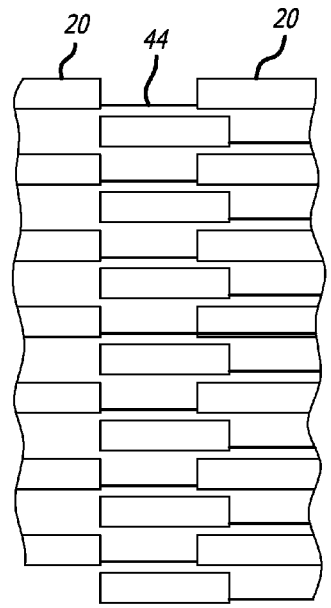

MULTI-ELECTRODE MAPPING CATHETER

CROSS REFERENCES TO RELATED APPLICATIONS

This application claims the benefit of U.S. Provisional Application No. 62/050,071, filed Sep. 12, 2014, incorporated herein by reference.

FIELD OF THE INVENTION

The invention relates generally to cardiac mapping, and more particularly, to a whole cardiac chamber, high density, multi-electrode mapping catheter adapted for cardiac endocardial contact mapping. At least a portion of the multi-electrode mapping catheter is formed from a flexible substrate. The multi-electrode mapping catheter can be utilized with a mapping system to provide instantaneous whole chamber voltage mapping of a heart chamber while enabling real time electroanatomic mapping utilizing a single heartbeat. The multi-electrode mapping catheter and its associated mapping system can be used with an ablation system to enable real time ablation mapping by depicting fully ablated areas on a graphical display to provide instantaneous feedback of ablation efficiency and to identify high value target ablation zones to the medical professional.

BACKGROUND

Cardiac arrhythmias involve an abnormality in the electrical conduction of the heart and are a leading cause of stroke, heart disease, and sudden cardiac death. Treatment options for patients with arrhythmia include medications, such as beta blockers, implantable devices, such as an implantable cardioverter-defibrillator (ICD), and catheter ablation of cardiac tissue.

Arrhythmias can be studied and diagnosed by "electrically mapping" the heart with catheters that are inserted through the patient's vasculature into a heart chamber. Cardiac endocardial mapping is a medical procedure by which electrograms, recorded directly from inside the heart chamber are used to characterize the heart conduction abnormalities. Generally, a mapping catheter can be inserted into the heart and used to map the electrical activity of the heart. The mapping catheter can be used to diagnose and/or treat heart disease. For example, maps can be used identify the origins of an arrhythmia to guide therapies, such as ablation, to treat the arrhythmia.

Contact mapping refers to an approach in which the electrodes are in direct contact with the heart wall. Electrodes are utilized for recording electrograms at different positions on the wall of a heart chamber, such as an atrium, so that various and important electrophysiological variables can be measured and analyzed from the electrogram recordings. Such variables include voltage potential, local activation times, fractionated voltage potentials, potential distribution during depolarization and repolarization, and vectorized data including conduction velocity and direction. Cardiac mapping is very important in locating aberrant conduction sites in the heart and the mapping catheter is frequently utilized to guide ablation. Various types of contact catheters have been developed that include catheters that are somewhat large and are designed to fill the entire heart chamber, or are smaller and need to be moved within the heart chamber to sequentially map various areas of the heart.

Endocardial mapping catheters have been of limited capability because they only have a few electrodes which makes it difficult to accurately map the heart. The most commonly used mapping catheters have multiple electrodes arranged along a single axis, typically ring electrodes encircling the catheter shaft at or near the distal end of the catheter, the portion of the device inside the heart.

In order to obtain a full chamber map it has been necessary to maneuver the distal extremity of the catheter extensively and to reposition it incrementally over the entire chamber of the heart. Such a procedure has been found to be time consuming and relatively inaccurate. Webster (U.S. Pat. No. 4,960,134) describes a symmetrical cylindrical control handle to enable accurate and precise catheter tip section movement. However, this improvement does not eliminate the need to maneuver across the endocardial surface to map a heart chamber. This method, called sequential contact mapping, does not provide a whole chamber map during a single cardiac cycle. In addition, a user must hold the catheter in position, often with his hand positioned awkwardly, making it difficult and inconvenient for a single operator to use separate mapping and ablation catheters. Ideally, the operator would be able to leave a mapping catheter in place without the need to position it with his hands so he/she can concentrate on maneuvering and positioning the ablation catheter. Ablation catheters have mapping capability, however, they only offer a few electrodes severely limiting their mapping utility.

Various attempts have been made over the years to provide arrays to map the cardiac walls. However, the use of undersized arrays of electrodes necessitates maneuvering the catheter in stepwise fashion across the entire endocardial wall, stopping at each increment to measure electrograms, then proceeding to the adjacent unmapped region until the whole chamber has been mapped in this manner. This method using an array of electrodes is called regional sequential mapping. It is not possible to create a whole chamber map in a single beat of the heart using this design. The regional mapping approach is time consuming. Moreover, in unstable arrhythmias such as atrial fibrillation, this design is inadequate to guide ablation.

Mapping catheter usually requires a sophisticated steering system to position and maneuver the catheter within the patient's vasculature and heart chamber, adding complexity and cost. Additionally, the steering apparatus is sometimes located within the lumen of the catheter thereby obstructing the lumen from other uses. Moreover, the operator will likely need to hold the mapping catheter in position to guide ablation, making it difficult for a single operator to map and ablate using two different devices. Thus, there remains an unmet need to provide a mapping catheter that increases electrode count, reduces complexity and cost, and provides for an instantaneous whole chamber map. Such a device should ideally be stable when positioned in the heart chamber to enable an operator to easily and quickly ablate tissue with a separate catheter.

As medical knowledge increases, catheterizations have become more complicated and more exacting. Today, most catheter ablation procedures are to treat atrial fibrillation. Most catheters used today were developed to treat simpler focal arrhythmias that tend to be very stable. However, when ablating atrial fibrillation or other complex macro-arrhythmias such as atrial flutter, these devices have significant limitations that result in long procedure times, poor outcomes, and an unacceptably high rate of complications.

Moreover, electrical abnormalities are usually diagnosed by mapping electrical activation paths along the endocardial surfaces of the heart chambers over time. The medical professional may place several catheters within one or more chambers of the heart to construct a map of sufficient detail to make an accurate diagnosis and to help determine ablation sites as part of a treatment strategy. Sometimes this electrical activity is cyclical, meaning it repeats beat after beat. In such cases, a simple mapping catheter with a linear set of electrodes may serve to perform the diagnosis by moving the catheter distal section to various regions and then point-by-point comparing activation times with a reference. The stability of the arrhythmia allows for this somewhat cumbersome technique. However, certain types of electrical activity within a heart chamber are not cyclical. Examples include atrial fibrillation. Such electrical activity is random. To analyze or map this type of electrical activity, all the points of the map must be obtained simultaneously. Moreover, since the chaotic nature of fibrillation has consequent effects throughout the chamber with respect to out-of-rhythm depolarizations, a view of the entire heart chamber is also beneficial.

Most mapping catheters utilize multiple components fabricated into discrete multi-electrode assemblies that can limit the number of electrodes that can practically be incorporated into the catheter. Each wire assembly adds unwanted stiffness to the catheter and the individual components can only be reduced in size to practical limits dictated by several factors such as assembly, machining capabilities, and strength requirements. Assembling individual components into a subassembly as described requires labor-intensive processes escalating the cost to manufacture such a device.

Another approach considered in the manufacture of mapping catheters is the use of flexible circuits, also known as "flex circuits." They consist of a thin insulating polymer film having conductive circuit patterns affixed thereto and typically supplied with a thin polymer coating to protect the conductor circuits. Polyimide is a common substrate material for a flex circuit but is typically thick imparting unwanted stiffness and poor resilience when used in a catheter. Also, when a flex circuit was used, it was often prone to kinking in the small curvatures required of an expandable array. Most, importantly, however, was that it was impractically expensive to form flex circuits of sufficient length to use in a catheter. Soldering individual wires to a flex circuit within the length of the catheter made for complicated and expensive manufacturing techniques. Multiple interconnections of flex circuits to other flex circuits or other components can increase the noise level along the circuit path, which can decrease the flex circuit's usefulness for detecting very low level electrical cardiac signals. While flex circuits have yielded some improvements in the circuitry field, flex circuit technology, while suggestive of potential, does not improve upon existing mapping catheter designs.

After the mapping catheter and associated system have identified the anatomic origin of the aberrant electrical conduction in the wall of the heart chamber, the medical professional may then proceed to ablate the offending tissue, thus treating the arrhythmia. Catheter ablation procedures have evolved in recent years to become an established treatment for patients with a variety of supraventricular and ventricular arrhythmias. The typical catheter ablation procedure usually utilizes targeted ablation of the site with an ablation device such as, but not limited to, a radio frequency (RF) catheter, that delivers a burst of high energy which affects the heart tissue by scarring the tissue to terminate the tissue's ability to allow natural electrical pulses to pass through aberrant conduction pathways. This procedure usually takes place in an electrophysiology laboratory and may last for several hours most of which is spent mapping the electrical conduction in the heart.

Although contact mapping catheters and systems are known in the art, there is a continuing need to improve the accuracy, stability, and maneuverability of such devices and systems so that they can be more widely used, especially as an adjunct to cardiac ablation procedures.

A need has also been recognized for an endocardial mapping catheter that incorporates a large number of electrodes making it possible to perform endocardial mapping accurately and rapidly and at a higher resolution, and that make possible simultaneous measurements of an entire chamber in the heart by providing electrode coverage over the entire area.

A further need has been recognized for a high electrode count within a shaft diameter compatible with typically used 8.5Fr trans septal delivery sheaths. Another need is for the ability to adapt the electrode carrying element, the splines, to conform to the heart chamber so the electrodes come into intimate contact with the heart wall while accommodating the wall motion of a beating heart.

Yet another need in the field is to be able to configure bipolar electrode pairs of sufficiently close spacing to precisely map areas of ischemia, where voltage potentials are low, areas of Complex Fractionated Atrial Electrograms (CFAE), and other anomalous regions with aberrant conduction patterns.

A still further recognized continuing need is to provide a system and method of the above character in which the electrodes are expanded into engagement with the wall of the chamber of the heart and are maintained in engagement with that wall during pumping action of the heart.

Still another need is for a system and method in which the electrodes are conformably retained in engagement with the wall forming the chamber of the heart during the time that the heart is expanding and contracting the chamber.

More needs include a device in which the presence of the distal extremity of the device; i.e., the mapping basket, in the heart does not substantially impede the flow of blood in the chamber of the heart. Additionally there is a need for a system and method of the above character in which the mapping and ablation procedures can be carried out without movement of the distal extremity of the catheter with respect to the wall forming the chamber of the heart.

And yet further needs exist for sufficient space between the splines of the basket to enable easy manipulation and positioning of an ablation catheter, and for a cost effective and densely packed interconnect method to route a large number of isolated electrical signal lines through a mapping catheter of a size accepted for use in these procedures. The invention fulfills these needs and others.

SUMMARY OF THE INVENTION

The present disclosure relates generally to a mapping catheter and, more specifically, to a mapping catheter device and methods for constructing at least a portion of the mapping catheter device on a flexible substrate.

In one particular aspect, the present invention is directed to a whole-cardiac-chamber, high-density, three-dimensional multi-electrode catheter adapted for cardiac endocardial contact mapping. The catheter utilizes an array of multiple electrodes arranged in a known spatial configuration that are placed on a flexible substrate to form an expandable basket (also referred to as a "frame") designed to conform to the target heart chamber so that the multiple electrodes come into intimate contact with the heart wall while accommodating wall motion of the beating heart. A placement of a large number of electrodes on the expandable basket makes it possible to perform endocardial mapping more accurately and rapidly and which make possible simultaneous measurements of an entire chamber in the heart by providing electrode coverage over the entire area. The use of a large number of electrodes over the target area provides the medical professional with a high resolution map of the heart chamber.

The endocardial mapping catheter of the present invention also makes it possible to perform endocardial mapping of the whole heart chamber based on a single heartbeat. The present invention will thus provide the medical professional with instantaneous mapping and re-mapping of the entire heart chamber on a beat-by-beat basis or in a single snapshot of time. The design of the present invention also allows for mapping and re-mapping of the target heart chamber while allowing simultaneous tissue ablation to be performed. Accordingly, the mapping catheter of the present invention can be incorporated with a mapping system that provides instantaneous feedback of ablation efficiency and can rapidly pinpoint high value target ablations zones to the medical professional.

In another aspect, the multi-electrode catheter includes a flexible expandable basket that has an array of electrodes forming a portion of a flexible circuit, often referred to as a "flex circuit" or "printed circuit" attached thereto.

The expandable basket can be formed into the shape of the target heart chamber where it will be deployed so that the multiple electrodes come into intimate contact with the heart wall while accommodating wall motion of the beating heart. The expandable basket is designed to move between a contracted, delivery configuration and a pre-shaped deployed configuration. The contracted configuration provides a low profile to the catheter to allow it to be advanced within the vasculature of the patient. Once the expandable basket is properly placed in the target heart chamber, it can be placed in its pre-shaped deployed configuration that allows the multiple electrodes to come into intimate contact with the heart wall. The flex circuit is affixed to a support layer which forms a portion of the expandable basket and is made from a material which is resilient and shapeable to the pre-shaped deployed configuration. The resiliency of the support layer allows the expandable basket to spring from its contracted configuration to its pre-shaped deployed configuration. In this regard, the expandable basket can be maintained in its contracted configuration by placing a retractable sheath co-axially over it to prevent the basket from expanding until the medical professional is ready to deploy the basket in the heart chamber. Once the expandable basket is properly positioned within the heart chamber, the medical professional need only to retract a proximal end of the restraining sheath to remove the sheath from the basket and allow it to deploy.

The flex circuit includes multiple conductors that are connected to the electrodes and are designed to communicate the signals received from each electrode to the mapping system to which the mapping catheter is connected. In this regard, the multi-electrode catheter includes a catheter shaft portion which extends from the expandable basket and also includes a flex circuit that extends along the length of the shaft to a proximal region (outside of the patient) where the flex circuit can be connected to the respective components of the mapping system.

In another aspect of the present invention, the catheter can be made from a long, single, continuous flex circuit which extends from the expandable basket and runs the length of the catheter shaft. This aspect creates a continuous conductive path from each electrode to the mapping instrumentation. In this regard, the flex circuit can be manufactured as a long flat component which can be selectively cut to form the size and shape of the expandable basket or any other configuration desired. The remaining uncut portion of the flex circuit is mounted along the catheter shaft portion of the catheter. This approach eliminates the needs for soldering electrical connections and for mechanical interconnections.

In an aspect according to principles of the invention, the use of a flex circuit mounted on the outside of the shaft portion of the mapping catheter creates a catheter structure in which an internal lumen running the length of the catheter shaft is not obstructed by the electrical conductors for the expandable basket, and is therefore available for other uses. This internal lumen can then be used to allow a secondary catheter, such as an ablation catheter of an ablation device, to be advanced therethrough into the heart chamber for ablation procedures while the electrodes arranged on the expandable basket remain in place against the wall of the heart chamber. This provides the medical professional with the ability to ablate the aberrant tissue in the heart chamber while obtaining continuous and instantaneous feedback from the mapping system of the ablation efficiency along with the targeting of high value ablation zones.

In other aspects, the flex circuit may be coiled in relation to the catheter shaft. Such configuration is believed to reduce rigidity of the catheter shaft. In another aspect, the flex circuit may be housed in a separate lumen in the catheter shaft. In yet another aspect, the flex circuit may be located within the catheter shaft.

In another aspect of the invention, the multi-electrode catheter can be manufactured utilizing two or more separate flex circuits which are electrically interconnected to form single, continuous conductors for each of the electrodes located on the expandable basket. In an aspect, a flex circuit is incorporated into the expandable basket of the catheter and is electrically and mechanically interconnected with another flex circuit that is mounted to the outside surface of the catheter shaft. In an aspect, the material forming the flex circuit associated with the expandable basket can be different from the material used to create the flex circuit associated with the catheter shaft. In another aspect, each of the various conductors formed on the flex circuit associated with the expandable basket is interconnected with an associated conductor of the shaft flex circuit utilizing a solderless connection. For example, an anisotropic conductive film (ACF) could be used to electrically connect the conductors of each flex circuit to each other after the conductors on each flex circuit have been properly aligned with each other. This electrically and mechanically interconnecting and bonding structure eliminates the need to hand solder each conductor of the basket flex circuit to its corresponding conductor on the shaft flex circuit. Accordingly, the use of the ACF to integrate the flex circuits together helps to lower manufacturing costs.

In one aspect of the invention, the expandable basket is cut into a portion of the flex circuit in the form of splines which have a plurality of electrodes longitudinally placed along the length of each spline. The number of splines, the spline width, and spline length can vary depending upon the size and shape of the heart chamber into which the expandable basket will be deployed, along with the number of electrodes which are to be placed on the expandable basket. The shaft flex circuit can be mounted to a bendable tubular member made from a material such as Pebax, or similar materials, which will provide the needed axial stiffness to the catheter shaft (referred to as "pushability") to allow the medical professional to advance the catheter within the patient's vasculature utilizing known Seldinger techniques.

In one particular aspect, the multi-electrode catheter can be made with fourteen individual splines with fifteen electrodes placed on each spline for a total of two-hundred and ten electrodes. The use of the flex circuit on the catheter made in accordance with the present invention allows the mapping catheter to be placed in a low profile contracted configuration, allowing it to be delivered through a standard 8.5Fr sheath into the left atrium. It should, however, be appreciated that the profile of the mapping catheter can be greater than 8.5 Fr in order to accommodate certain ablation catheters. Upon exiting the sheath, the expandable basket has inherent resilience to expand and conform to the chamber of the heart it is placed because of the use of a new design construct. The basket can be adapted to match the human atrium and will be offered in 45 mm, 55 mm, and 65 mm diameters (expanded). It can be made of an all polymer composite, eliminating the need for a nitinol support. Alternatively, the expandable basket can be made with both polymer and nitinol components. This construction provides for optimal electrode to endocardial wall contact, a very important performance parameter needed to obtain high density and high fidelity electrograms. Alternatively, push/pull wires can be associated with the expandable basket to allow the user to manually change the size (diameter) and shape of the expanded basket, as needed.

The foregoing and other advantages of the present invention will become more apparent to those skilled in the art to which the present disclosure relates from the following description of the present invention and the accompanying exemplary drawings.

BRIEF DESCRIPTION OF THE DRAWINGS

The foregoing and other features of the invention will become apparent to those skilled in the art upon reading the following description of preferred embodiments with reference to the accompanying drawings, in which:

FIG. 6 is a side view showing the splines with attached electrodes which form the expandable basket disclosed in FIGS. 3-5;

FIG. 7 is a cross-section view of the flexible shaft of FIG. 6 showing the outer layer as being a flex circuit, the next layer inward being a tubular body member having a large primary lumen and a smaller secondary lumen located within the primary limen, the secondary lumen having a size for use of a pull wire or a push rod;

FIG. 8 is a plan view of one particular embodiment of a flex circuit (in a flattened state) used to form the expandable basket sub-assembly of a mapping catheter embodying features of the present invention;

FIG. 9 is a plan view of the flat flex circuit disclosed in FIG. 8 after further processing;

FIG. 10 is a plan view of the flex circuit disclosed in FIG. 9 after the flex circuit has been rolled into a tubular shape to form the expandable basket sub-assembly;

FIG. 11 is an exploded side elevational view showing the various layers forming the flex circuit associated with the expandable basket along with the support layers which are affixed to the flex circuit;

FIG. 12 is a side longitudinal sectional view showing the connection of the electrodes of the flex circuit to the various conductors located on different metallic layers which cooperate to form the flex circuit;

FIG. 13 is a plan view which shows the subsets of electrodes which are connected to the various conductors of the multiple metallic layers forming the flex circuit;

FIG. 14 is a plan view showing the trace conductors of the fourth metallic layer which connect to the electrodes;

FIG. 15 is a plan view showing the electrodes disposed over the trace conductors shown in FIG. 14;

DETAILED DESCRIPTION OF THE PREFERRED EMBODIMENTS

Figure 1:
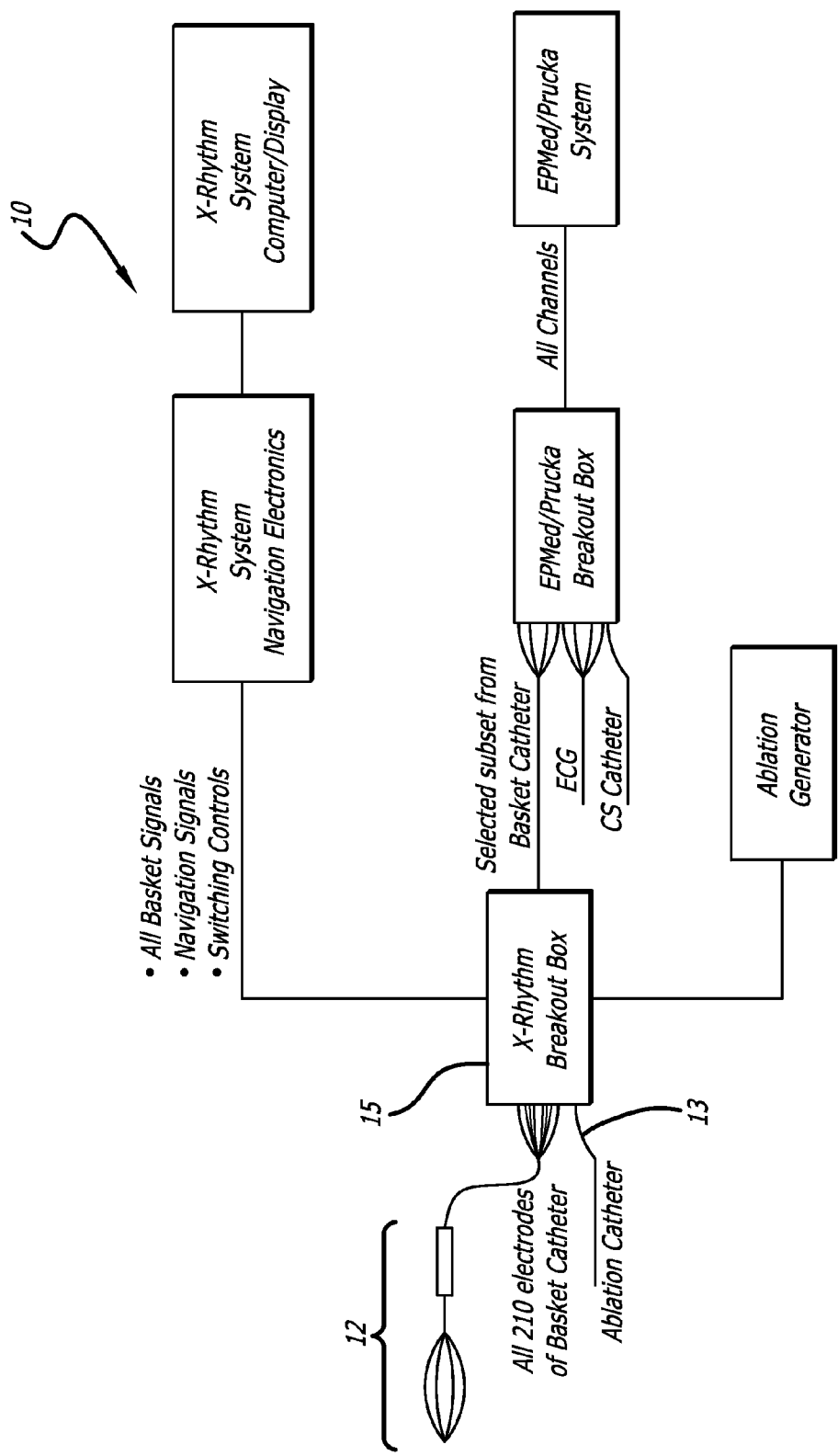
FIG. 1 is a schematic illustration of an endocardial mapping and ablation system which can incorporate a multi-electrode cardiac mapping catheter that embodies features of the present invention.
Figure 2:
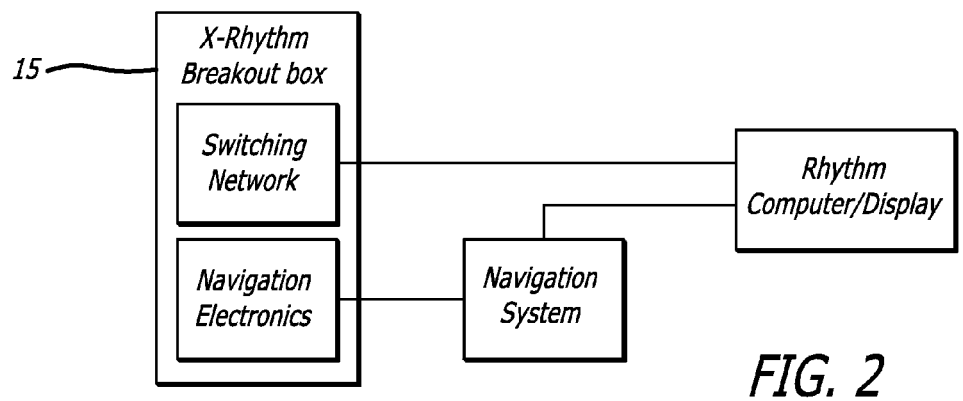
FIG. 2 is a schematic illustration of a navigation system which form a part of the mapping and ablation system depicted in FIG. 1.

Turning now in more detail to the drawings in which like reference numerals indicate like or similar elements across the several views, FIGS. 1 and 2 schematically depict a endocardial mapping and ablation system 10 which incorporates a multi-electrode mapping catheter 12 which embodies features of the present invention. The mapping catheter 12 (described in greater detail below) and an ablation catheter 13 are connected to the system through a breakout box 15 (similar to the CIM or catheter input module of the Carto® system or the Nay modules of the NavX™ system). The breakout box serves to route all signals to the main system, as needed, while allowing user selected signals to be forwarded to the EP system, as well as connecting the ablation generator to the ablation catheter 13. The system's mapping function uses the cardiac signals detected from the heart surface via electrodes located on the mapping catheter 12 to create a real time, three dimensional (3D) activation map or circuit map, either static or animated, which can be viewed on the computer display. This allows the medical professional to visualize the wave of depolarization activity across the whole heart chamber.

The system's navigation function uses an impedance-based method of locating the mapping catheter 12 within the catheter chamber. The mapping catheter may utilize an opposing pair(s) of electrodes located on the expandable basket of the catheter as directional reference electrodes. The system additionally reads the relative voltages of the electrodes located on the ablation catheter (which is roaming within the heart chamber) as well as all (or a select few) of the electrodes of the mapping catheter. This allows the system to compute the positions of the electrodes on the ablation catheter relative to the positions of the electrodes of the mapping catheter 12. The medical professional may then navigate the ablation tip of the ablation catheter to the desired location utilizing the generated activation map or other map in order to apply treatment (ablation) to the aberrant conductive tissue of the wall of the heart chamber.

In real time, the activation map or other map is regenerated to show the resulting efficacy of the ablation procedures which have been provided to the wall of the heart chamber. A combination of the two allows the medical professional to (1) measure/map electrical activity on the heart surface in order to detect/visualize arrhythmias, (2) navigate the ablation tip of the ablation catheter to the desired location in order to apply treatment (ablation of the target tissue), and (3) re-measure/electrical activity of the heart surface again to inspect the results of the ablation. This re-measurement/ mapping of the electrical activity of the heart can be performed on a beat-by-beat, or a single snapshot, basis for the whole heart chamber.

The mapping catheter includes a conductive distal end 14 (e.g., with conductors and insulators). The conductors can be associated with one or more sensors. In some instances, the conductors can be configured to accept the one or more sensors.

The conductors and insulators (and, in some cases, other additive elements, such as sensors) can be printed on a flexible substrate. In some instances, the conductors and insulators can be printed on the flexible substrate as individual entities within a single layer. In other instances, the conductors and insulators can be printed layer-by-layer onto the flexible substrate to form a multi-layer configuration.

The flexible substrate material printed with the conductors and insulators can be very flexible. In some instances, the flexible substrate material can include a malleable material that is soft and pliable. An example of a malleable material that can be soft and pliable is a polymer. In some instances, the polymer can be a thermoplastic (e.g., polyether ester keytone (PEEK)). The flexible substrate printed with the conductors and insulators can be bendable, can resist kinking, and can be both conductive and insulating.

One particular embodiment of a mapping catheter 12 incorporating features of the present invention has a conductive distal end which includes an expandable basket 14 that is movable between a contracted configuration (FIG. 5) and a pre-shaped deployed expanded configuration (shown in both FIGS. 3 and 4) and is constructed with a plurality of flexible splines 16. The mapping catheter 12 can remain in its contracted position (FIG. 5) by utilizing a retractable sheath (not shown) which would extend co-axially over the expandable basket 14. The expandable basket 14 can be placed into its expanded configuration (FIG. 3) by simply retracting the sheath from the collapsed basket 14. The resiliency of the expandable basket 14 would propel it into the expanded configuration once the sheath has been retracted.

Each spline has a flex circuit 18 (described in greater detail below) affixed to its outer surface which includes a number of sensors, hereinafter referred to as electrodes 20, that are longitudinally distributed along the length of each spline. The flex circuit provides each electrode 20 with a conductor which extends to the proximal end 28 of the catheter. The longitudinal distribution of the electrodes 20 along each spline 16 need not be uniform as is shown in the disclosed embodiment of the multi-electrode catheter 12 but may be selectively controlled in order to achieve the overall distribution of electrodes 20 needed in the target heart chamber. For example, electrodes 20 located near the distal end 22 of the composite basket 14 could be distributed more densely than in other locations of the expandable basket 14. It should be appreciated that any desirable electrode distribution along the splines 16 forming the expandable basket 14 may be accomplished through selective placement of the electrodes 20 on the flex circuit.

Figure 5:
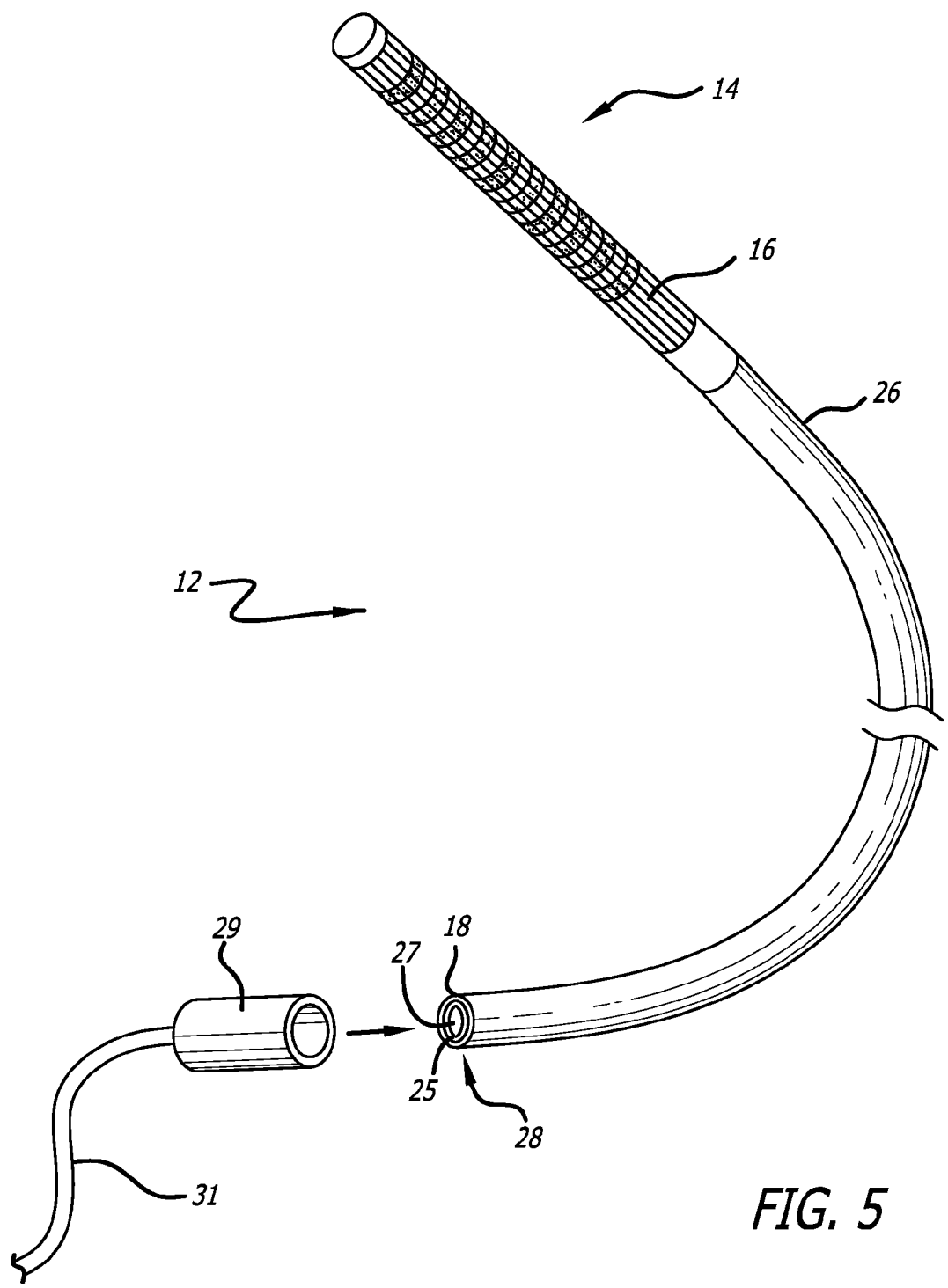
FIG. 5 is a perspective view of the mapping catheter of FIG. 4 with the expandable basket placed in its contracted configuration, also showing a connector at the proximal end of the catheter shown removed from the catheter in this view to permit clarity of illustration.

In the embodiment of FIGS. 5 and 6, a connector 29 is shown to be attached at the proximal end 28 of the catheter shaft. The connector 29 has been moved to the left for the purpose of showing the internal configuration of the catheter shaft. In actual use, the connector would be attached to the proximal end of the catheter shaft and would make connection with the flex circuits, depicted by cable 31 in FIGS. 5 and 6. The connector would be used to transition the signals conducted by the flex circuits to a separate connector that would then receive the signals conducted by the flex circuits for further processing outside the catheter. The connector 29 can take different forms, one of which is a zero insertion force connector.

Figure 3:
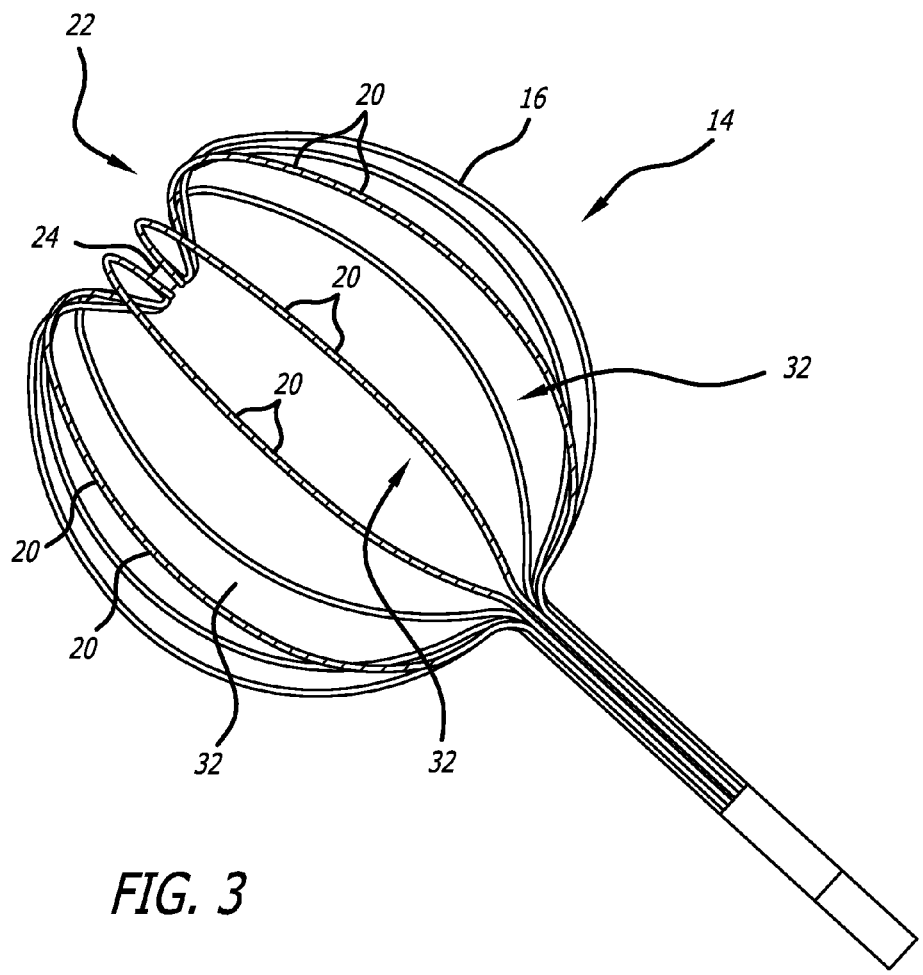
FIG. 3 is a perspective view of an expandable basket of a multi-electrode mapping catheter embodying features of the present invention.

As can best be seen in FIGS. 3 and 6, the pre-shaped deployed configuration of the expandable basket 14 subassembly is designed to replicate the size and shape of the heart chamber in which the basket 14 is to be deployed. The distal end 22 of the basket 14 is specially designed to include a depressed "pocket" or "recess" which is formed to allow the distal most electrodes 20 on each spline to come into better contact with the wall of the heart chamber. An end cap 24 can be attached to the distal end of the basket 14 to maintain the integrity of the distal ends of the individual splines 16 as the basket 14 may be required to deploy and collapse numerous times during the ablation procedure. The other electrodes 20 can be spaced accordingly on each of the splines 16 to maximize the area of the heart chamber to be mapped. The end cap 24 may be rounded so as to avoid any damage to tissue with which it may come into contact.

Figure 4:
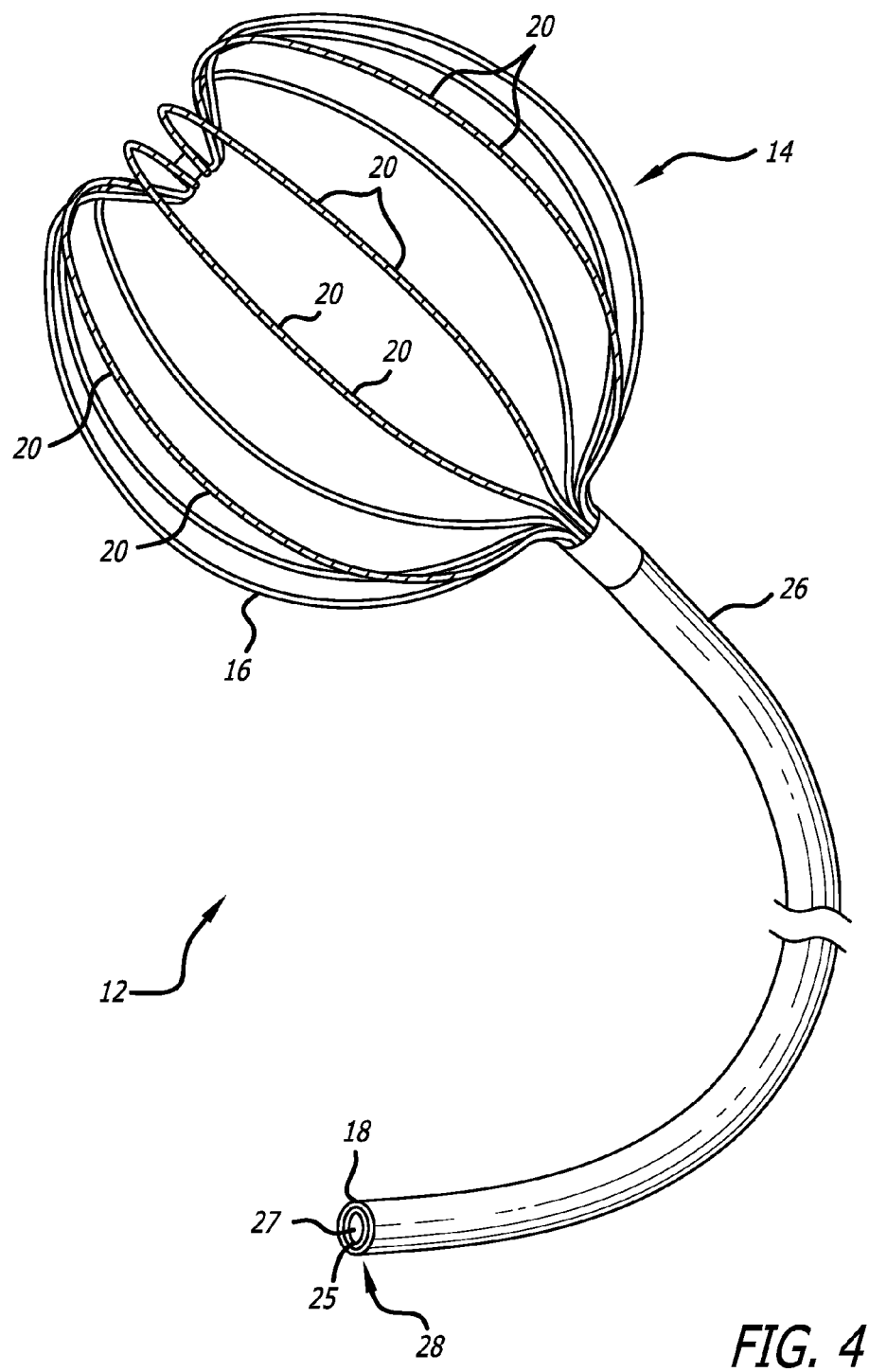
FIG. 4 is a perspective view of a multi-electrode cardiac mapping catheter embodying features of the present invention with its expandable basket in its pre-shaped deployed configuration.

A flexible catheter shaft 26 extends from the expandable basket 14 to a proximal end 28. As can be seen in FIGS. 4 and 5, the flexible catheter shaft 26 includes a tubular body member 25 having an unobstructed central lumen 27 formed therethrough for receiving and positioning a distal ablation tip of an ablation catheter within the expandable basket 14 in order to allow the medical practitioner to selectively perform tissue ablation to the aberrant conduction sites which have been detected and mapped by the present invention. The unobstructed central lumen 27 of the mapping catheter 12 also can allow for simultaneous insertion and use of regional mapping or ablation tools. Accordingly, the central lumen 27 is free to accept other instruments besides an ablation catheter, such as, for example, a regional mapping catheter or other medical tools.

Referring now to FIG. 7, an alternative arrangement of the flexible shaft 26 is shown with the outer layer as being the flex circuit 18 with the tubular body member 25 having both a unobstructed central lumen 27 therethrough for receiving a medical device such as an ablation catheter and a secondary lumen 33 having a size for receiving a pull wire or push rod 35. The distal end (not shown) of the push rod would be connected, for example, to the distal end of the expandable basket with the proximal end (not shown) of the rod extending outside the patient during the catheter mapping procedure. The user of the mapping catheter would manipulate the proximal end of the push rod axially to change the position of the distal end of the basket, and hence, the size and shape of the basket.

The flex circuit 18 is preferably affixed to the outside surface of the tubular body member 25 to maintain the sufficiently large central lumen 27 for receiving the ablation catheter. The tubular body member 25 provides a flexible, but supporting, structure to provide the mapping catheter 12 with sufficient pushability to allow the expandable basket 14 to be advanced into the target heart chamber. Suitable materials for the tubular body member 25 include, but are not limited to, polyether block amide (PEBAX®). The proximal end 28 of the catheter shaft can be electrically attached to a device (not shown) which allows the mapping catheter 12 to be coupled to the instruments of the mapping system and provides a suitable opening to the catheter lumen 27 to allow an ablation catheter to be inserted therein.

As can be seen in FIGS. 3 and 5 which show the expandable basket 14 in its deployed configuration, spaces 32 between each spline 16 provide an ample opening in which the distal ablation tip of an ablation device can be positioned to ablate the desired aberrant wall tissue of the heart chamber. The flex circuit affixed to the splines 16 of the expandable basket 14 continues from the basket 14 and extends along the flexible shaft to create a multiplicity of continuous leads which extend from the electrodes 20 and run the length of the catheter shaft. The portion of the flex circuit which runs along the length of the catheter shaft is often referred to hereinafter as the "shaft flex circuit." The use of the shaft flex circuit opens up an internal lumen in the mapping catheter which most prior art mapping catheters use for routing conduction wires and/or deployment mechanisms from the expandable basket 14 to the proximal end 28 of the mapping catheter. Accordingly, prior art mapping catheters, lacking a sufficiently large inner lumen, were unable to receive an ablation catheter for placement of its ablation tip within the expandable basket 14 for ablation while the expandable basket 14 remains fully deployed and capable of measuring, re-measuring and recording electrograms on the wall of the heart chamber on a beat-by-beat basis. The present invention thus provides a mapping catheter 12 which is unmatched in its ability to provide the medical professional with information and mapping and re-mapping on a real time basis while performing the ablation procedure.

The flex circuit 18 located on the expandable basket 14 is rather thin and requires to be affixed to a support layer 34 (See FIGS. 11 and 12) made from a flexible substrate material which is both resilient and shapeable to allow the splines 16 to be set into their pre-shaped deployed configuration. Suitable materials for this support layer 34 include thermoplastic polymers such as polyether ether ketone (PEEK) and PEBAX® which are materials that can be readily heat set to the pre-shaped deployed configuration using heat setting techniques well known in the art. Other suitable materials which provide the resiliency to allow the splines 16 to move from the contracted delivery configuration to the pre-shaped deployed configuration also could be used. Shape memory materials, for example, Nitinol, could be used.

A longitudinal sectional view of the basket flex circuit, depicted in FIGS. 11 and 12, shows a first metallic layer 36 which forms the multiple electrodes 20 and a plurality of stacked, metallic layers 38, 40 and 42, each metallic layer including a plurality of conductors 44, often referred to as signal traces. Each electrode 20 of the first metallic layer 36 is connected to one of the conductors 44 of the plurality of metallic layers 38, 40, and 42. The conductors 44 of the flex circuit associated with the basket assembly 14 can extend to the proximal end 28 of the catheter shaft 26 or can be interconnected to corresponding conductors 44 formed on the shaft flex circuit. The particular arrangements of the shaft and basket flex circuits are further discussed below.

FIG. 5 shows the expandable basket 14 of the mapping catheter 12 in its contracted configuration which allows the medical professional to advance the catheter through the patent's vasculature and into the target heart chamber. While the expandable basket 14 remains in its contracted configuration, the splines 16 lie together alongside each other in a roughly tubular shape as can be seen in FIG. 5. Again, a retractable restraining sheath (not shown) which would be co-axially placed over the splines 16 of the expandable basket 14 to maintain an inward force on each spline 16 to prevent the basket 14 from moving into its pre-shaped deployed configuration. The splines 16 are made from a resilient material which urges each spline 16 to move into its set shape that has been imparted on the expandable basket 14. Once the expandable basket 14 is properly positioned in the heart chamber by the medical professional, the proximal end of the restraining sheath, which remains outside of the patient during the procedure, can be retracted proximally to remove the retraining sheath from contact with the splines 16 to allow each spline 16 to expand radially outward into the pre-shaped deployed configuration. Each spline 16 is self-expanding which allows the spline 16 to move generally outwardly in a radial direction to attain the pre-shaped deployed configuration as is shown in FIG. 4. Once the medical procedures have concluded, the medical practitioner can simply move the proximal end of the restraining sheath distally to allow the restraining sheath to contact the splines 16 and move them back into their contracted configuration. The mapping catheter 12 can then be easily removed from the heart chamber and patient's vasculature since the will remain in its contracted configuration. The diameter of the mapping catheter 12 (with restraining sheath) should be about 8.5 French or less when the expandable basket 14 is placed in its contracted configuration. This diameter will readily allow the mapping catheter 12 to be advanced through the patient's vasculature.

In the particular catheter 12 shown in FIGS. 3-7, the splines 16 of the expandable basket 14 may carry various sets of independent electrodes 20. In the disclosed embodiment, the expandable basket 14 may include fourteen individual splines 16, each spline having a total of fifteen electrodes 20. Accordingly, the multi-electrode catheter 12 will have some two hundred and ten (210) sensing electrodes 20 distributed over and along the various splines 16 to provide ample coverage within the heart chamber. Several locator electrodes (not shown) may be affixed to some of the splines 16 and positioned diametrically opposed to each other to assist in identifying the locations of the various electrodes 20 when placed within the heart chamber.

In summary, the flexible substrate which forms the basket 14 can printed with the conductors and insulators can be (1) bonded with the catheter as a sub-assembly with the printed conductors and insulators; or (2) used as splines of an expandable frame with the printed conductors and insulators (e.g., each spline can be made of the flexible substrate material that includes a plurality of electrodes and a plurality of insulators). In either case, at least the conductors can be printed on the surface of the polymer material of the flexible substrate. The additive elements can be printed on the material of the spline so that they are configured to minimize interference with the free expansion and collapse of an expandable frame.

In some instances, the expandable frame or basket can be made with a plurality of expandable splines made, at least in part, of the flexible substrate. For example, the splines of the expandable basket can be pliable, allowing the basket to expand from a compressed form to an expanded form once it reaches a target area (e.g., a chamber of the heart and/or a blood vessel). In some instances, the expandable basket can be configured to conform to the individual anatomy of the target area when in the expanded form (e.g., to maximize sensor-tissue contact).

The expandable basket can be designed to be larger than the open volume of the target area to ensure full and complete contact with the target area. In some instances, further expansion/contraction of the basket can be accomplished via a pull wire or push rod. In other instances, the expansion can be accomplished via a sliding sheath mounted coaxially on the catheter. In further instances, the basket can be shaped using heat above room temperature and below the melting temperature of the material to heat set the expandable basket to a shape that can mimic the shape of the target area.

Method of Manufacture

Figure 18:
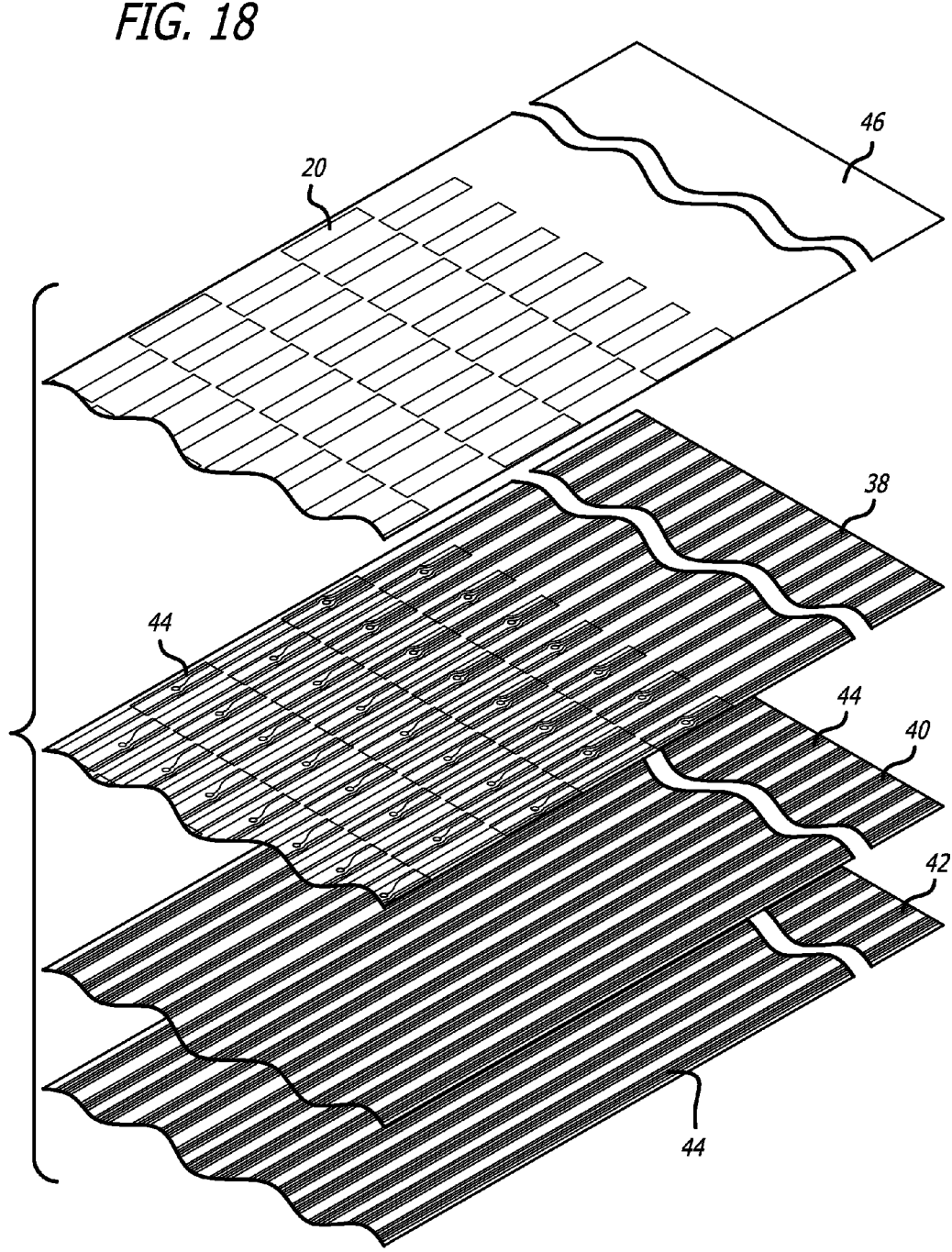
FIG. 18 is an exploded view showing portions of the various layers which form a flex circuit which can be used to manufacture a mapping catheter embodying features of the present invention.
Figure 19:
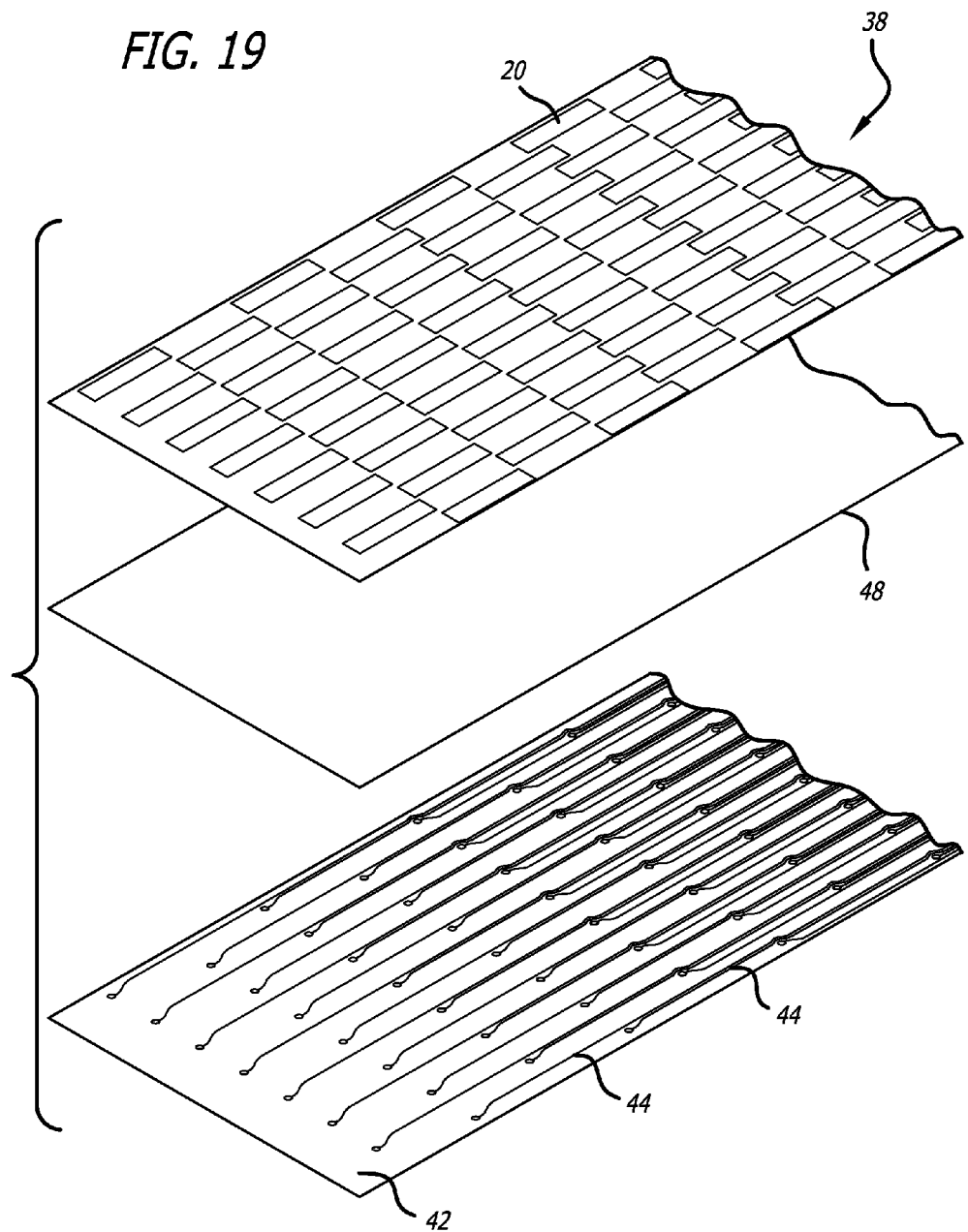
FIG. 19 is an exploded view showing portions of the other various layers which form a flex circuit which can be used to manufacture a mapping catheter embodying features of the present invention.
Figure 20:
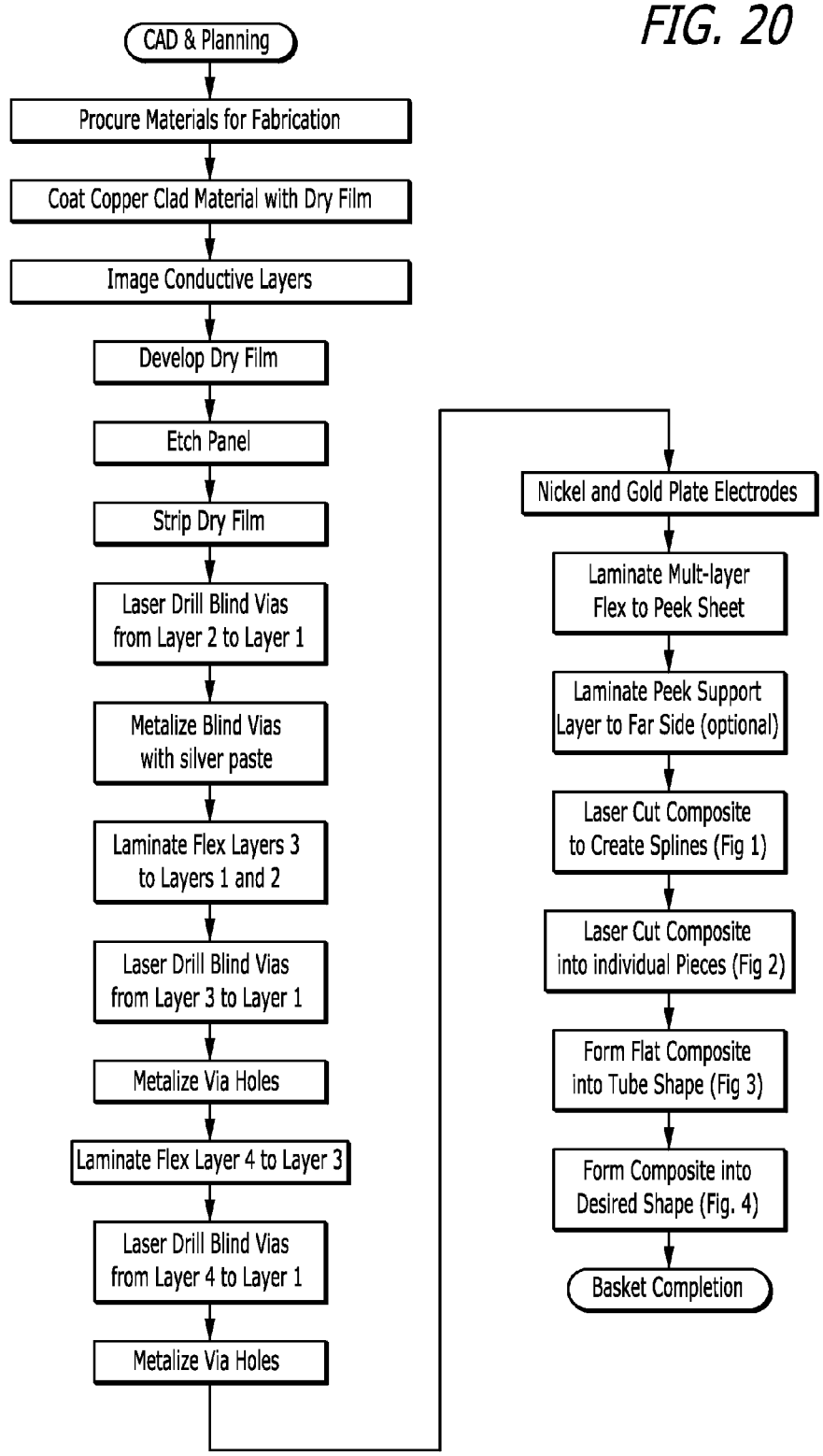
FIG. 20 is a process flow diagram illustrating a method for forming a flex circuit having a multi-layered construction of electrodes, conductors, and insulators in accordance with an aspect of the present invention.

FIGS. 8-19 show the detailed construction of a particular flex circuit 18 and FIG. 20 provides the sequence of processing steps which could be utilized to manufacture the flex circuit 18. It should be noted that the various metallic layers, insulating layers and adhesive layers are not drawn to scale. Some layers described are very thin while others are thicker. As can be seen in FIG. 11, the flex circuit include a first or top metallic layer 36 which forms the electrodes 20 (not all shown) that are disposed on the splines 16 of the expandable basket 14. These electrodes 20 are deposited on an insulating layer 46 which is made from a polyimide or other suitable insulating material. For example, the insulating layer 46 could be manufactured from a liquid crystal polymer. This first metallic layer 36 can be copper or other suitable metal which forms the pad of the electrode 20. This pad can be later plated with gold and/or nickel to enhance the electrical conductivity of the electrode 20. It should be appreciated that the size, shape and projection height of the individual electrodes can be varied, as needed, to facilitate proper endocardial contact.

The flex circuit 18 further includes multiple metallic layers 38-42 which are printed or otherwise deposited on the insulating layers so as to form multiple conductors 44 (traces) which are electrically connected to the electrodes 20. A second metallic layer 38, which forms conductors 44 (traces), is deposited on the opposite side of the top insulating layer 46. A third metallic layer 40 and fourth metallic layer 42 form multiple conductors 44 which are connected to select electrodes 20. Each of the third and fourth metallic layers 40 and 42 is printed onto an insulating layer 46 which serves to insulate the various metallic layers from each other. Adhesive layers 48 are utilized to affix the various metallic layers to an adjacent insulating layer.

FIGS. 11 and 12 also show a support layer 34 which is applied over the bottom of the flex circuit 18 to provide rigidity and a resilient medium which allows the splines 16 to be set to the pre-shaped deployed configuration. The support layer 34 may have various thickness and material compositions in order to achieve the desired rigidity of the flex circuit in order to control the deployed shape. The exemplary support layer 34 of the invention comprises a 10 mils (250 um) thick polyimide. It should be appreciated that other materials such as PEEK may be used as a support layer. The support layer 34 is adhered to the to the bottom of the flex circuit using a polyimide adhesive layer 48. Other adhesives, and in particular, pressure sensitive adhesives may also be used for this purpose. Additional support layers 50 may be applied over the support layer to further increase the stiffness of the basket in select regions.

Generally, the insulating layers 46 which form the flex circuit have a thickness of about 0.5 mils (12.5 µm). The same is true for the adhesive layers 48 and metallic layers 36-42 used to form the flex circuit. As is mentioned above, the PEEK support layer 34 can have a thickness of about 10 mils (250 µm). The thickness of this support layer 34 will depend on the physical characteristics of the material selected. The additional support layer 50 can have a thickness which can vary depending on the material selected. For example, this additional support layer 50 could be made from a polymeric material such as PEBAX®. While the additional support layer 50 is shown being affixed to the PEEK support layer 34 utilizing an adhesive material, it should be appreciated that these two support layers 34 and 50 can be heat bonded together. Alternatively, other shape memory material, such as Nitinol, could be incorporated into the expandable basket to provide added resiliency to the basket.

The individual splines 16 of the basket assembly are formed, separated, and differentiated from each other using precise slits 52 which define the width and length of the various splines 16 formed on the flex circuit 18. The slits 52 are simply thin gaps that are cut in the flex circuit 18 using one of many cutting techniques that may include laser cutting, die cutting or chemical etching. The slits of the exemplary flex circuit are cut using a laser so as to position the position of the slit precisely. The cutting of the slits 52 is usually performed while the flex circuit 18 remains in its flatted manufactured condition (as is shown in FIG. 8) since more precisely formed slits 52 can be achieved. However, the cutting of the slits also could be performed when the flex circuit is placed in its tubular shape.

The electrodes 20 are connected to the desired conductor 44 utilizing metalized vias 54 which extend from the electrode 20 to the location of the conductor 44 to which the particular electrode is to be electrically connected. As can be seen in FIG. 12, one electrode 44 is shown electrically connected to the second metallic layer 38 by a metalized via 54 which extends through the insulation layer 46. An adjacent electrode 20 is, in turn, electrically connected to a conductor 44 formed on the third metallic layer 40 by a metalized via 54 which extends through two insulation layers 46 and an adhesive layer 48. A third electrode is shown electrically connected to the fourth metallic layer 42 utilizing a metalized via 54 which extends through three insulation layers 46 and a pair of adhesive layers 48. The conductors 44 on each of the metallic layers are arranged such that a metalized via 54 does not extend through a conductor 44 located between the electrode 20 and its corresponding conductor 44.

FIG. 13 shows how the conductors 44 of the multiple metallic layers can be arranged with the electrodes 20 to avoid the possibility of having metalized vias 54 extend though other conductors located on intermediate metallic layers. FIG. 13 shows three subset of the electrodes 20 which are arranged to be electrically attached to certain conductors of the stacked metallic layers without interfering with other conductors. The first subset of electrodes 20 formed on the distal most portion of the flex circuit 18 and located at the distal most end of the expandable basket 14 have been circled with a dashed line marked with the reference numeral 56. FIG. 19 shows an exploded view of the various layers of the flex circuit at this particular region. These electrodes 20 are connected to the conductors 44 located on the fourth metallic layer 42, which forms the bottom most metallic layer on the flex circuit 18. The conductors 44 formed on this fourth metallic layer 42 extend to each of the longitudinally spaced electrodes 20 in this distal most region. As can be seen in FIGS. 14, 15 and 19, all of the conductors 44 on the fourth metallic layer 42 (and all of the other metallic layers) include a connector pad 45 (the circular element formed at the end of each conductor 44) which is used to connect the electrode to that particular conductor (utilizing the metalized via). The various conductors 44 formed on this fourth metallic layer are sufficiently spaced apart from each other to prevent the metalized via from touching an adjacent conductor or one of the connector pads. Also, none of the other metalized vias in the other locations of the flex circuit are formed deep enough to contact a conductors formed on the fourth metallic layer. FIG. 14 shows a portion of the fourth metallic layer with a few of the more distally extending conductors 44 with their connecting pads 45. FIG. 15 shows the placement of the electrodes 20 over the various pads depicted in FIG. 14.

Figure 16:
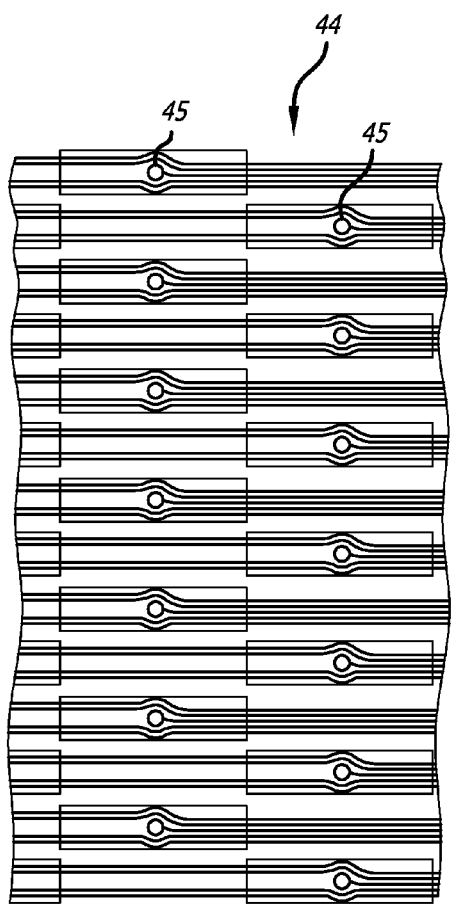
FIG. 16 is a plan view showing the trace conductors of the second metallic layer which connect to the electrodes.
Figure 17:
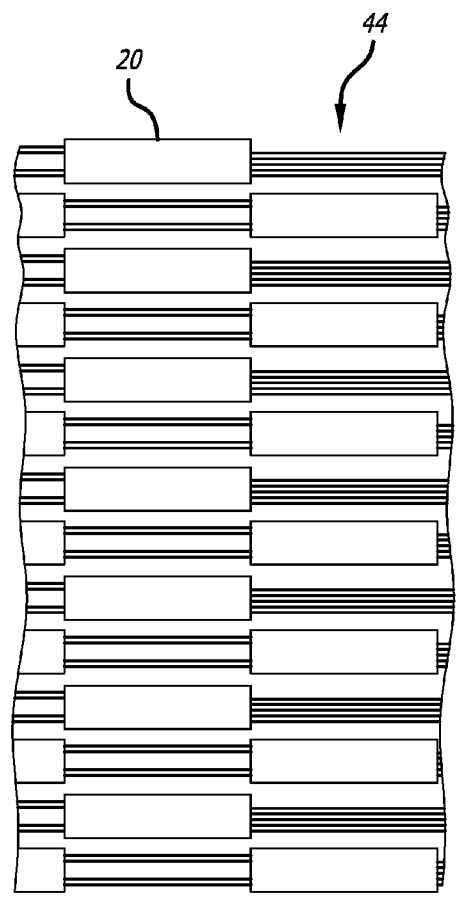
FIG. 17 is a plan view showing the electrodes disposed over the trace conductors shown in FIG. 14.

A second subset of electrodes 20 are located on the center portion of each spline and have been circled with a dashed line with the reference numeral 58 in FIG. 13. This set of electrodes 20 are designed to be electrically connected to the conductors 44 of the third metallic layer 40. The proximal most set of electrodes 20 on the flex circuit 18 have been circled with a dash line and designated with the reference numeral 60 in FIG. 13. This proximal set of electrodes 20 is designed to be electrically connected to the conductors 44 of the second metallic layer 38. As in the exploded view shown in FIG. 19, FIG. 18 shows the various metallic and insulation layers found in the region designated by the dashed lines marked with the reference numeral 60 in FIG. 13. These electrodes can be found at the proximal region of the flex circuit 18 and likewise are placed on the more proximal region of each spline. It should be appreciated that the second metallic layer in FIG. 18 has been turned upside down since the second metallic layer 38 is actually formed on the underside of the top insulation layer 46. This figure may give the false impression that another layer has been added to the stack of layers forming the flex circuit 18. However, the additional "second metallic layer" appearing in FIG. 18 merely provides the reader with a view of how the various conductors 44 and pads 45 are laid out on the second metallic layer 38 at this proximal region of the flex circuit. FIG. 16 shows a portion of the second metallic layer with a few of the more distally extending conductors 44 with their connecting pads 45. FIG. 17 shows the placement of the electrodes 20 over the various pads depicted in FIG. 16. FIGS. 14 and 16 show the layout of a typical trace pattern which could be used on the metallic layers to prevent crossover of the formed traces. Such trace patterns utilized on these metallic layers are well known in the art.

As is shown in FIGS. 8-11, the flex circuit 18 includes a proximal segment 62 which extends beyond the cut splines 16 formed in the distal portion of the flex circuit 18 which is formed into the expandable basket. This proximal segment contains the conductors 44 (traces) which run to the proximal end 63 of the segment 62. The length of this proximal segment 62 can vary depending on whether the mapping catheter 12 is manufactured utilizing a single flex circuit 18 or if a separate flex circuit is connected to a separate shaft flex circuit. When a single flex circuit 18 is employed, the distal portion of the flex circuit is initially fabricated with the support layers and cut to form the expandable basket. The basket can then be formed into shape. Thereafter, the proximal segment of the flex circuit 18 can be "rolled" onto and bonded, for example, to the outside surface of the tubular body member which forms a portion of the catheter shaft.

Figure 21:
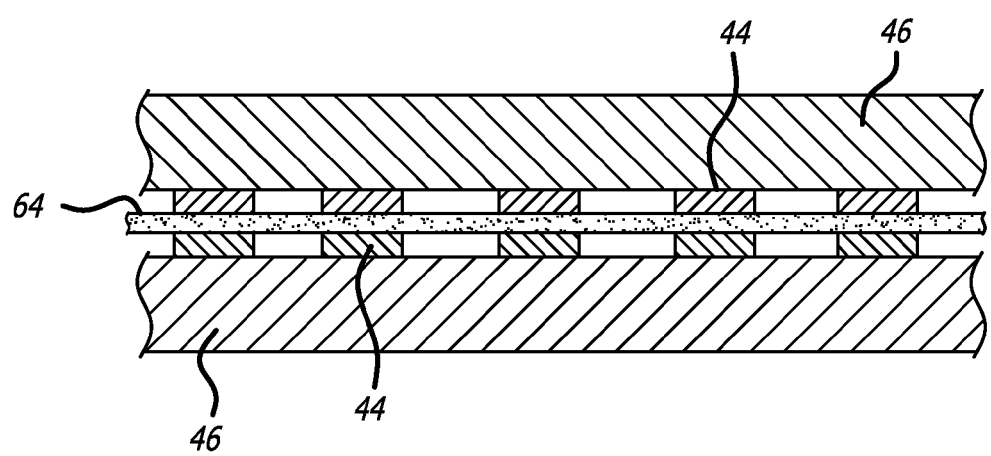
FIG. 21 is a cross sectional view showing the connection of conductors of the basket flex circuit to conductors of the shaft flex circuit utilizing a tie layer of anisotropic conductive film.

When two separate flex circuits are utilized to form a composite flex circuit, after the basket sub-assembly has been fabricated, the conductors 44 of each metallic layer must be connected to corresponding conductors 44 of the shaft flex circuit. The numerous conductors of each metallic layer extend will be exposed at this proximal segment 62 to provide a surface to which the conductor of the shaft flex circuit will be bonded. In this particular embodiment, the length of the proximal segment 62 does not have to extend very long since the shaft flex circuit would have sufficient length to run from the expandable basket to the proximal end of the catheter shaft. Likewise, the shaft flex circuit will have a segment which includes exposed conductors which correspond to the conductors located on the basket flex circuit. The conductors of the metallic layers of the shaft flex circuit are designed to overlap the exposed conductors of the basket flex circuit. The connection of conductors of the basket flex circuit to the conductors of the shaft flex circuit will utilize a tie layer 64 of anisotropic metallic film which is conductive in Z-axis only to eliminate the need for hand soldering of individual interconnects. A major component of the labor costs in high density electrode catheters is in the hand soldering of individual electrodes 20. FIG. 21 shows one particular method for connecting the conductors formed on each of the basket flex circuit and shaft flex circuit.

One particular method for bonding the shaft flex circuit to the basket flex circuit as follows:

1. The basket sub-assembly is initially fabricated and the basket 14 is set into its pre-shaped configuration. The proximal segment of the basket flex circuit containing the interconnect bond sites will remain unprocessed and hence retains its flattened state.

2. The shaft flex circuit is affixed to the tubular body member made by "rolling" the flattened flex circuit onto the member then bonded. The bonding could be performed with adhesive bonding materials or the layers could be heat fused together.

3. The distal extremity of the flex circuit overhangs the distal segment of the catheter shaft.

4. The distal extremity of the shaft flex circuit extends past the catheter shaft and remains in flat state.

5. The bond sites of the flat proximal segment 60 of the basket flex circuit and corresponding flat flex circuit (distal end of the shaft flex circuit) are aligned so that the corresponding circuit bond sites are in vertical alignment with a tie-layer of ACF. (See FIG. 21 which schematically shows conductors 44 of the basket flex circuit vertically aligned with corresponding conductors 44 of the shaft flex circuit and bonded together utilizing a tie layer 64 of ACF).

6. The aligned site are exposed to heat and/or pressure to electrically connect intended bond interconnects (1 to 1, 2 to 2, 3 to 3, 209 to 209, 210 to 210) without causing inadvertent short circuits between adjacent circuit paths 7. Once the bond is made, the flattened joined sections of the basket flex circuit and the shaft flex circuit are fused into a tubular shape.

8. An inner support segment made from Pebax or similar material is inserted and fused into place to support the now bonded structures and to provide additional tensile strength to the catheter shaft.

9. Alternatively, both the basket flex circuit and shaft flex circuit are formed into a tube. The two mating surfaces are aligned with one designed to fit over the other. Fiducial markers including locating holes may be placed to aid alignment. Pins may be used to maintain alignment of the basket 14 to shaft bond sites. A tubular form of an ACF may be used to electrically connect the corresponding bond sites.

Figure 22:
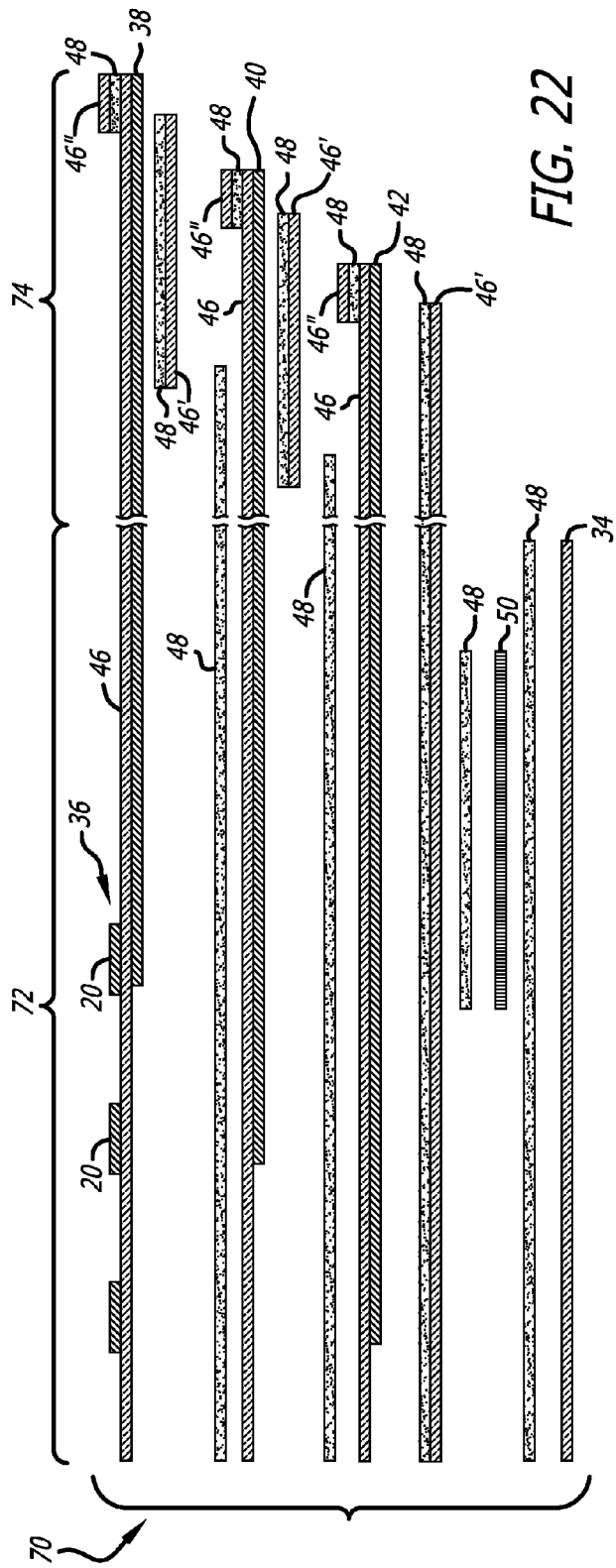
FIG. 22 is a side longitudinal sectional view showing the connection of the electrodes of the flex circuit to the various conductors located on different metallic layers which cooperate to form a flex circuit having a long length and which embodies features of the present invention that include a portion which form the basket assembly along with a continuous length that forms proximal portion of the catheter.
Figure 23:
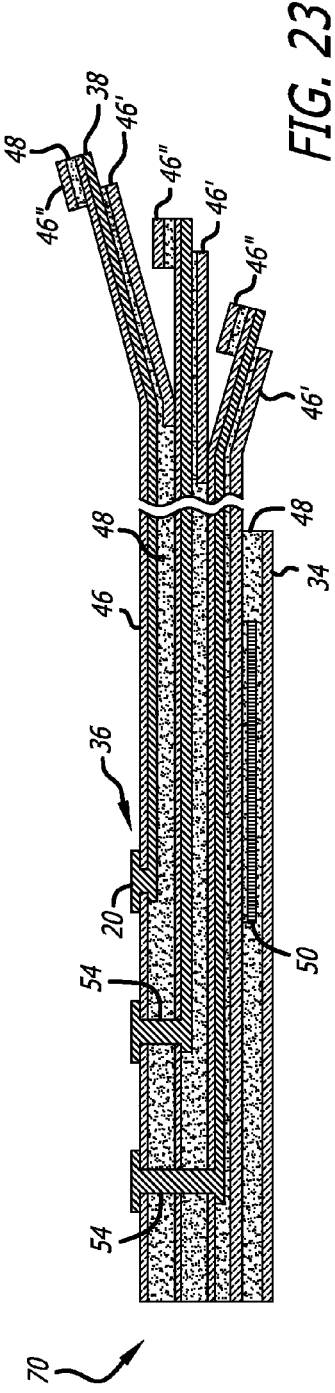
FIG. 23 is a side longitudinal sectional view showing the connection of the electrodes of the flex circuit to the various conductors located on different metallic layers which cooperate to form the flex circuit depicted in FIG. 23.

Another particular embodiment of a flex circuit which can be used to form the multi-electrode catheter is disclosed in FIGS. 22 and 23. This particular embodiment utilizes the same type of electrodes, conductors and insulating layers disclosed in the embodiment of FIGS. 3-19. This embodiment utilizes a single flex circuit 70 which can be fabricated to extend from the distal basket to the proximal end of the catheter shaft. This structure would eliminate the need to bond two flex circuits together which should further reduce manufacturing costs. Such a structure would eliminate the need for the anisotropic conductive film connection as is shown in FIG. 20.

The flex circuit 70 disclosed in FIGS. 22 and 23 shows a distal portion 72 which is formed into the expandable basket and a long proximal segment 74 which will constitute the shaft flex circuit and will run the length of the catheter shaft. Accordingly, the distal segment 72 of the such a flex circuit would be cut to form the splines 16 of the basket while the proximal segment 74 remains in its uncut, flattened condition. The proximal segment 74 can then be affixed to the tubular body member which forms a portion the catheter shaft.

Referring initially to FIG. 22, the flex circuit 70 include a first or top metallic layer 36 which forms the electrodes 20 (not all shown) that are disposed on the splines of the expandable basket. These electrodes 20 are deposited on an insulating layer 46 which is made from a polyimide or other suitable insulating material. This first metallic layer 36 can be copper or other suitable metal which forms the pad of the electrode 20. This pad can be later plated with gold and/or nickel to enhance the electrical conductivity of the electrode 20. It should be appreciated that the size, shape and projection height of the individual electrodes can be varied, as needed, to facilitate proper endocardial contact.

The individual splines which will be cut into the distal region 72 of the flex circuit 70 can be formed using the same or similar techniques disclosed above. The slits which are formed in the distal region 72 of the flex circuit 70 can also be cut using a laser so as to properly position the slits which will be cut into the flex circuit 70. The cutting of the slits 52 is usually performed while the flex circuit 18 remains in its flatted manufactured condition since more precisely formed slits can be achieved. However, the cutting of the slits also could be performed when the flex circuit is placed in its tubular shape. The proximal region 74 of the flex circuit 70 can be rolled onto the tubular body member with an internal lumen to form the shaft portion of the catheter. The internal lumen allows for the passage of other instruments, such as an ablation catheter, from the proximal end of the catheter shaft to the distal region 72 of the flex circuit 70 where the expandable basket is formed.

The flex circuit 70 further includes multiple metallic layers 38-42 which are printed or otherwise deposited on the insulating layers so as to form multiple conductors (traces) which are electrically connected to the electrodes 20. A second metallic layer 38, which forms conductors (traces), is shown deposited on the opposite side of the top insulating layer 46. A third metallic layer 40 and fourth metallic layer 42 form multiple conductors 44 which are connected to select electrodes 20. Each of the third and fourth metallic layers 40 and 42 is printed onto an insulating layer 46 which serves to insulate the various metallic layers from each other. Adhesive layers 48 are utilized to affix the various metallic layers to an adjacent insulating layer.

A bottom support layer 34 made from a flexible material such as PEEK is in turn adhesively bonded to the flex circuit 70 to provide the substrate used to form the expandable basket. Alternatively, an optional support layer 50 may be placed between the flex circuit 70 and PEEK support layer to aid bending by minimizing conductor fractures. Adhesive layers bond the various support layers 34 and 50 to the distal region 72 of the flex circuit 70.

All of the electrodes 20 are shown disposed on the first insulating layer 46. The top conductor (formed from the first metallic layer 38) is shown directly beneath this first insulating layer 46 which extends from the first electrode to a proximal end of the flex circuit 70. The conductor becomes encapsulated by a second insulting layer 46' which extends from the distal region 72 of the circuit 70 to the proximal end of the proximal region. As can be seen in FIGS. 22 and 23, an adhesive layer 48 is used to bond the second insulating layer 46' to the first insulating layer 46. At the proximal end, a short insulating layer 46" is adhesively fixed to the first insulating layer 46 via an adhesion layer 48 to provide additional rigidity to the composite catheter which will be created from this flex circuit 70.

The second set of conductors of metallic layer 40 is also adhesively attached to a second insulating layer 46'. This second set of conductor extends to the proximal end of the flex circuit and has an insulating layer 46" adhesively attached to the end of the flex circuit.

The third set of conductors of metallic layer 42 is also adhesively attached to a second insulating layer 46' and has an additional insulating layer 46" attached at the proximal end of the flex circuit 70.

Referring specifically to FIG. 23, the use of vias 54, as disclosed in the FIG. 12 allows the individual electrodes located on the outer surface of the circuit 70 to be connected to their respective conductors. The proximal end of the flex circuit 70 allows a zero insertion force ("ZIF") connector (not shown) to be connected to the individual conductors (traces) located at the proximal end of the flex circuit 70. The ZIF connector can be used to connect up to 210 conductors depending upon the design features.

The support layer 34 which is applied over the bottom of the flex circuit 70 to provide rigidity and a resilient medium which allows the splines 16 to be set to the pre-shaped deployed configuration. The support layer 34 may have various thickness and material compositions in order to achieve the desired rigidity of the flex circuit in order to control the deployed shape. The exemplary support layer 34 of the invention comprises a 10 mils (250 um) thick PEEK. It should be appreciated that other materials such as PEEK may be used as a support layer. Nitinol is another example of a support layer with heat settable properties to control shape. The flex circuit may use, for example, a polyimide adhesive layer for bonding the various components together. Other adhesives, and in particular, pressure sensitive adhesives may also be used for this purpose.

Generally, the insulating layers 46 which form the flex circuit 70 shown in FIGS. 22 and 23 have a thickness of about 0.5 mils (12.5 μm). The same is true for the adhesive layers and metallic layers used to form the flex circuit, although an adhesive layer of about 1 mils (250 μm) could be used when the optional support layer is adopted. As is mentioned above, the PEEK support layer 34 can have a thickness of about 10 mils (250 μm). The thickness of this support layer 34 will depend on the physical characteristics of the material selected. The additional support layer 50 can have a thickness which can vary depending on the material selected. For example, the additional support layer 50 could be made from a polymeric material such as PEBAX®. While the additional support layer 50 is shown being affixed to the PEEK support layer 34 utilizing an adhesive material, it should be appreciated that these two support layers 34 and 50 could be heat bonded together.

Figure 24:
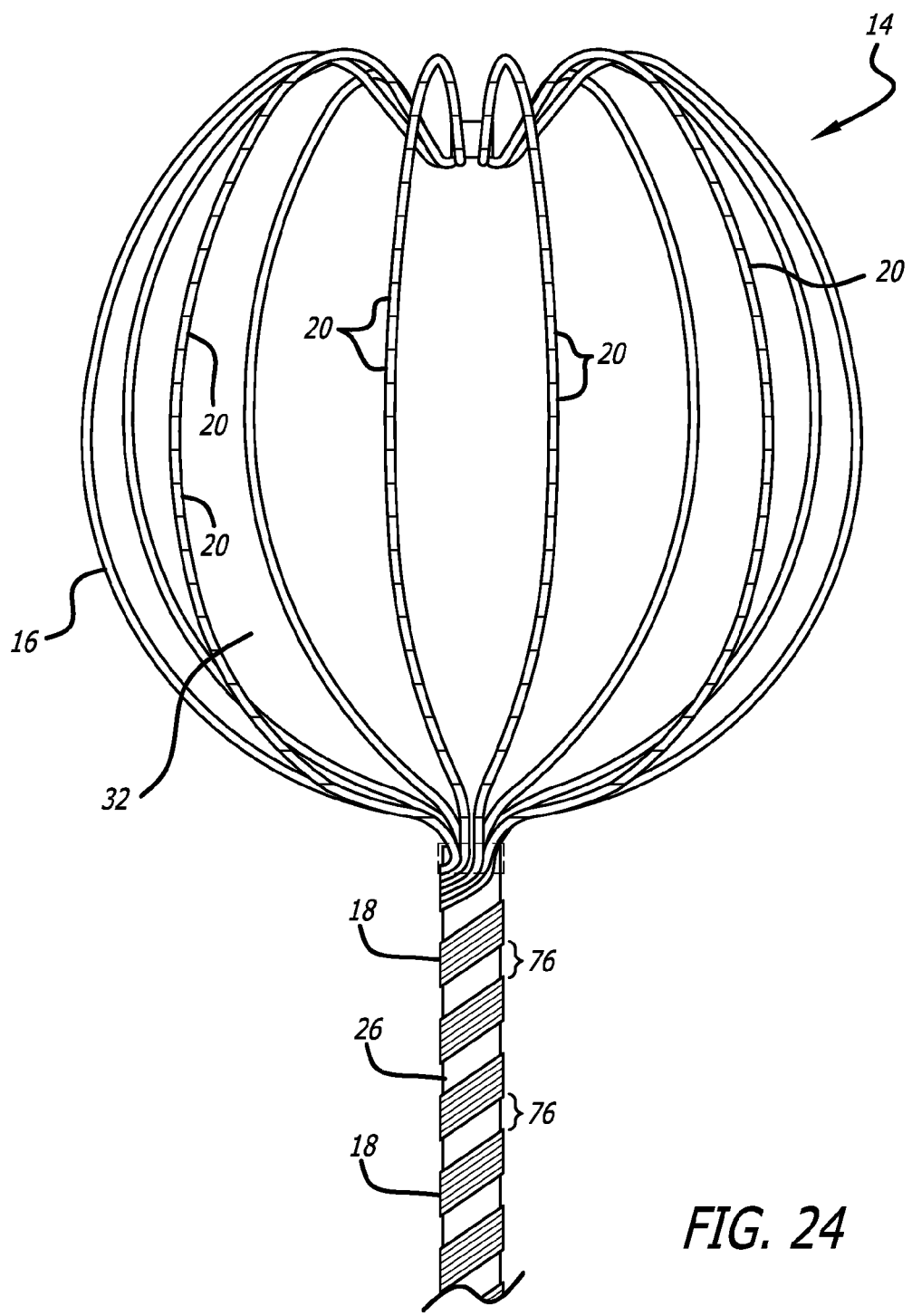
FIG. 24 is a side view of the expanded and deployed basket of a multi-electrode mapping catheter similar to that illustrated in FIG. 3 showing the flex circuit coiled around the outside of the catheter shaft.

FIG. 24 shows an alternative embodiment of a multi-electrode mapping catheter which includes a flex circuit 18 coiled about the outside of the tubular body member 25 that forms a portion of the proximal catheter shaft. As can be seen in FIG. 23, the flex circuit 18 extends around the tubular body member 25 such that there are spaces 76 formed between "turns" of the flex circuit 18 to provide additional flexibility to the catheter shaft. While FIG. 23 shows the spacing of the flex circuit 18 somewhat exaggerated for illustration purposes, the principle of this placement of the flex circuit 18 onto the outer surface of the tubular body member 25 is intended to show one structure which may provide added flexibility in the proximal shaft of the mapping catheter 12.

Thus there is provided a whole chamber high definition mapping catheter and method for manufacture and use. The present invention provides for quick and accurate identification of target areas for ablation. The invention provides the means to reliably map unstable arrhythmias. Additionally, there is instantaneous feedback of ablation efficacy.

The present invention thus provides a catheter with an expandable and contractible frame comprising printed conductors and insulators adapted for accepting sensors or electrodes (collectively referred to as "sensors" for convenience). The disclosed catheter can be optimized to conform to an individual anatomy to maximize sensor-tissue contact. The expandable frame and additive elements can be optimized to conform to the chamber of a heart or vessel to maximize sensor contact as described above. The sensor (electrode) printed on the catheter helps to minimize interference of the free expansion and collapse of the frame. An insulating layer printed on a conductive layer (sensor, electrode) also helps to minimize interference of the free expansion and collapse of the frame (basket). Alternatively, more than one frame or basket can be generally positioned on the distal end of the catheter. The splines or struts of the basket can be made entirely of a polymer and can be optimized to conform to its surroundings which may be a chamber of the heart (like an atrium) or a vessel. The catheter can be made with a series of printed electrodes applied directly to the polymer surface. The electrodes are connected to the proximal end through either printed interconnects or configured as an assembly where the interconnects applied to the expandable basket are then connected from the proximal end to the distal expanded portion with a separate interconnect. The electrodes and interconnects may be selectively insulated using a printing technology. The electrode and insulators can be stacked in multi-layer configuration. The expandable frame or basket can be expanded or collapsed by a sliding sheath mounted coaxially on the catheter. Alternatively a pull wire can be used. In an embodiment disclosed above, the basket is biased into an expanded configuration. Upon sliding the outer sheath in the proximal direction, it is moved off the basket allowing the basket, due to its bias, to spring outwardly into contact with the target tissue. In another embodiment, there may be more than one expandable frame each containing its own set of electrodes. Sensor, as used herein, can be an electrode, thermocouple, ultrasound transducer, pressure sensor for example.

The expandable basket allowing for large spaces to optimize use with ablation catheters, where the ablation device can be positioned between frame elements. The expandable basket elements can be optimized to prevent interference of ablation. It is anticipated that there will be used for a catheter with multi-layer printing without an expandable basket.

An alternative approach to create a subassembly made of circuit conductors uses special processes to print circuit conductors, insulators, and sometimes a multilayer set of conductors and insulators on a very flexible substrate. This completed circuit subassembly is then bonded directly to the catheter. The fused circuit conductor assembly and catheter having desirable characteristics, bendable, resistance to kinking, conductive where intended and insulating where intended. The circuit printing technology is well suited to print on a curved member like a catheter shaft.

The expandable basket can be designed to be larger than the open volume defined by the anatomy. The basket design and catheter is configured to expand to completely contact the anatomy by employing a malleable polymer structure with printed circuits that preserve the soft pliability of the polymer. For configurations using a pull wire, having a spring attached between the handle pull knob (lever, etc.) and the pull wire. The spring constant selected so that it stretches when the expandable basket makes full and complete contact with the open volume of the destination. Similarly, expanding the basket when using a sliding sheath, the oversized frame (relative to the open volume of the destination) is matched to optimally engage the electrodes to the destination wall. The expandable basket elements can be optimized for the particular anatomy to prevent excessive exertion of force against the destination wall. Sensors, such as, for example, force or pressure sensors, may be embedded in the expandable basket or distal region of the catheter to advance physiological readings to the proximal region of the catheter via the conductors.

The expandable basket can be independently rotated via a dedicated control. This control is optimized to function whether the frame is fully expanded or partially expanded.

This is achieved using highly lubricious coating (hydrophilic) on the basket or alternatively on the sheath and the opposing contact surface.

DEFINITIONS

In the context of the present disclosure, the singular forms "a," "an," and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "mapping catheter" can generally refer to a tubular member which can be inserted into the chamber of the heart that can be associated with one or more electrodes. In some instances, the electrodes map the electrical activation of the heart.

As used herein, the terms "expandable basket" or "expandable frame" can refer to a device at the distal end of the mapping catheter that can include one or more electrodes. The basket or frame can be collapsed to a contracted position when the cardiac mapping catheter is advanced through the patient's vasculature and moved into a preshaped deployed configuration when the catheter reaches its target destination (e.g., within a chamber of the heart).

As used herein, the term "spline" can refer to a slat, a strut, or a portion of the expandable basket. In some instances, a spline can be a strut of a basket-shaped expandable element.

As used herein, the term "conductor" can refer to a material or device that transmits or conducts electricity, heat, sound, or other energy. In the electronic field, a "signal trace" or "trace" on a printed circuit board is the equivalent of a wire for conducting signals and constitutes a "conductor" as used herein. The trace may consists of a flat, narrow part of a metallic material, such as copper, that remains on an insulating layer after etching. Signal traces are usually narrower than power or ground traces because their current carrying requirements are usually much less. There are numerous known ways of creating a trace in the art.

As used herein, the term "sensor" can refer to a device that detects or measures a physical property and records, indicates, or otherwise responds to the physical property. Examples of sensors can include, but are not limited to a thermocouple, an ultrasound transducer, and a pressure sensor. In this case the word "sensor" is also meant to refer to an "electrode" for convenience. In some instances a conductor can be associated with a sensor.

As used herein, the term "interconnect" can refer to a material and/or a device that can be used to connect two things together. In some instances, an interconnect can connect two conductors in series. In other instances, an interconnect can connect one or more conductors to a receiver.

As used herein, the term "insulator" can refer to a material used for insulation that does not readily transmit or conduct electricity, heat, sound, or other energy, depending on the application.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein but their intended meaning is the same.

As used herein, the term "medical professional" can refer to any person involved in conducting a medical procedure utilizing the mapping catheter described herein including, but not limited to, physicians, medical students, nurse practitioners, nurses, and other operating room staff.

As used herein, "flexible circuit" or "flex circuit" refers to an array of conductors (sometimes referred to as "traces" herein) bonded to a thin dielectric film. Flexible circuits are typically composed of at least one metal layer such as copper (Cu), nickel (Ni), tin (Sn), silver (Ag) or gold (Au) on a flexible polymeric film such as polyester (PET), polyimide (PI), or liquid crystal polymer (LCP). For high performance applications, the primary metal layer is commonly copper while the film layer is usually polyimide.

As used herein, "anisotropic conductive film" ("ACF"), is a is an epoxy or acrylic adhesive system used by electronics industry to make electrical and mechanical connections from drive electronics to substrates. Anisotropic conductive adhesives, commonly known as "Z-axis" adhesives, are conductive in the Z-axis and are non-conductive in the X- and Y-axis. Anisotropic conductive film (ACF) which consists of an adhesive epoxy matrix and randomly distributed conductive particles are widely used as the connection material for electronic devices with high input/output counts. Anisotropic conductive films (ACFs), more appropriately referred to as anisotropic conductive adhesive films (ACAFs), have been introduced as a promising flip chip interconnection material, due to its potential in achieving high density VO interconnection, low processing temperature and relatively mild impact on the environment. In particular, devices with flip chip on flexible substrate (FCOF) using ACFs are now widely used in smart cards, disk drives and driver chips for LCDs.

While the present invention has been described herein in terms of certain preferred embodiments, those skilled in the art will recognize that modifications and improvements may be made without departing from the scope of the invention. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

We claim:

1. A multi-electrode mapping catheter for endocardial contact mapping of a heart chamber of a patient, the mapping catheter comprising:
   a flexible elongated catheter shaft having a proximal end, an outer surface, and a distal end;
   an expandable mapping basket located at the distal end of the catheter shaft, the expandable mapping basket including a plurality of spaced-apart flexible splines, each flexible spline including a flex circuit affixed to a support layer made from a flexible substrate material, the flexible substrate material being resilient and shaped to bow outwardly to bias the basket to an expanded configuration for deployment for mapping by which the expandable mapping basket maintains the flex circuit in contact with the wall of the heart while accommodating wall motion of the beating heart;

wherein each flex circuit includes a first layer having a plurality of electrodes formed thereon and a metallic layer, the metallic layer including a plurality of conductors, each electrode of the first layer being connected to a separate conductor of the metallic layer, wherein the electrodes are located so as to be at an outer surface of the flex circuit and in contact with a wall of the heart chamber when deployed; and wherein each flex circuit comprises a continuous single-piece electrical conductor that is directly in electrical contact with an electrode and that is mounted to the outer surface of the catheter shaft and extends along the entire elongated catheter shaft without interruption and without interim connection to any other electrical device and which terminates at the proximal end of the catheter shaft to thereby directly communicate signals received at the respective electrode to the proximal end of the catheter shaft.

2. The multi-electrode mapping catheter of claim 1 wherein the flex circuits are coiled about the outer surface of the catheter shaft.

3. The multi-electrode mapping catheter of claim 1, wherein the conductors of the metallic layer of the flex circuit are printed onto an insulating layer which forms a portion of the flex circuit.

4. The multi-electrode mapping catheter of claim 1, wherein the flexible substrate material comprises a thermoplastic polymer.

5. The multi-electrode mapping catheter of claim 4, wherein the thermoplastic polymer comprises polyether ether ketone (PEEK).

6. The multi-electrode mapping catheter of claim 1, wherein:
the catheter shaft comprises a lumen having a size large enough to permit passage of an ablation catheter; and
the flexible splines are spaced apart by a distance that is greater than the size of the ablation catheter;
whereby the ablation catheter may be extended from the distal end of the catheter shaft and between the mapping basket into contact with the heart chamber so that ablation may be performed simultaneously with mapping.

7. The multi-electrode mapping catheter of claim 1, wherein all flex circuits are formed together on the same flexible substrate with the spline portion of each flex circuit being differentiated from other spline portions by longitudinally-extending slits.

8. The multi-electrode mapping catheter of claim 7, wherein: the catheter shaft comprises a second lumen having a size large enough to permit passage of an ablation catheter; and
the flexible splines are spaced apart by a distance that is greater than the size of the ablation catheter;
whereby the ablation catheter may be extended from the distal end of the catheter shaft and between the mapping basket into contact with the heart chamber so that ablation may be performed simultaneously with mapping.

9. A multi-electrode mapping catheter for endocardial contact mapping of a heart chamber of a patient, comprising:
an expandable basket movable between a contracted configuration and a pre-shaped deployed configuration, the expandable basket including a plurality of flexible splines, each of the plurality of flexible spines including a flex circuit affixed to a support layer made from a flexible substrate material, the flexible substrate material being resilient and shapeable to the pre-shaped deployed configuration, each flex circuit including a first layer having a plurality of electrodes formed thereon and a plurality of metallic layers, at least one metallic layer including a plurality of conductors, each electrode of the first layer being connected to one of the conductors of the plurality of metallic layers, wherein the expandable basket maintains the electrodes in direct contact with the wall of the heart while accommodating wall motion of the beating heart;

an elongated flexible catheter shaft extending from the expandable basket, the catheter shaft having a distal end connected to the basket, an outer surface, and a proximal end, and the flexible catheter shaft having a lumen formed therethrough for receiving and positioning a distal end of an ablation catheter within the expandable basket for simultaneous mapping and ablation of a heart chamber; and a catheter shaft flex circuit having a plurality of metallic layers, at least one of the shaft metallic layers including a plurality of conductors formed thereon, the catheter shaft flex circuit being mounted to the outer surface of the flexible catheter shaft and extending along the entire length of the elongated flexible catheter shaft to its proximal end, and is connected to a flex circuit associated with the expandable basket by means of a solderless connection.

10. The multi-electrode mapping catheter of claim 9, wherein each conductor of the flex circuit associated with the expandable basket is solderlessly bonded to a corresponding conductor of the shaft flex circuit.

11. The multi-electrode mapping catheter of claim 10, wherein each conductor of the flex circuit associated with the expandable basket is solderlessly bonded to a corresponding conductor of the shaft flex circuit by a tie layer of anisotropic metallic film.

12. The multi-electrode mapping catheter of claim 9, wherein the conductors of each conductor layer of the flex circuit are printed onto an insulating layer which forms a portion of the flex circuit.

13. The multi-electrode mapping catheter of claim 9, wherein the flexible substrate material is a thermoplastic polymer.

14. The multi-electrode mapping catheter of claim 13, wherein the thermoplastic polymer is polyether ether ketone (PEEK).

15. The multi-electrode mapping catheter of claim 9, wherein the metallic layers of the flex circuit extend to the proximal end of the catheter shaft.

16. A method for performing an ablation procedure in a heart chamber of a patient, comprising:
advancing a cardiac mapping catheter having an expandable basket movable between a contracted configuration and a pre-shaped deployed configuration and which is attached to a distal end of a flexible elongated catheter shaft, the catheter shaft having a lumen sized to receive an ablation catheter of an ablation device to position a distal tip of the ablation catheter within the expandable basket, the flexible elongated catheter shaft having an outer surface, and a proximal end, the expandable basket having a plurality of electrodes on an outer surface for receiving voltage readings in a chamber of the heart;
deploying the expandable basket into the pre-shaped deployed configuration within the heart chamber;

obtaining whole-chamber voltage readings in the heart chamber utilizing the mapping catheter and conducting the received voltage readings to the proximal end of the catheter shaft by means of a flex circuit comprising a continuous single-piece of electrical conductors that are directly in electrical contact with respective electrodes, the flex circuit being mounted to the outer surface of the catheter shaft and extending along the entire elongated catheter shaft without interruption and without interim connection to any other electrical device, and which terminates at the proximal end of the catheter shaft to thereby directly communicate voltage readings received at the respective electrodes to the proximal end of the catheter shaft;

ablating an aberrant conductive site within the heart chamber by advancing an ablation device between splines of the basket;

simultaneously receiving whole-chamber voltage readings in the heart chamber as ablation of the aberrant site is being performed; and simultaneously receiving whole chamber voltage readings in the heart chamber after ablation of the aberrant site has been performed.

17. The method of claim 16, wherein the step of conducting received voltage readings comprises conducting such readings to the proximal end of the catheter shaft through the flex circuit in which the entire flex circuit has been affixed to a support layer prior to cutting splines in the electrode section of the flex circuit to connect with electrodes.

18. A medical catheter comprising:

an elongated flexible catheter shaft having a proximal end, an outer surface, and a distal end;

a medical device located at the distal end of the catheter shaft adapted to sense a biological parameter of a patient and provide electrical signals representative of the sensed biological parameter;

an electrical catheter shaft connector located at the proximal end of the catheter shaft adapted to provide electrical signals provided by the medical device at the catheter shaft connector so that such signals may be conducted to a complementary connector that is electrically engaged with the catheter shaft connector; and an elongated flex circuit comprising a continuous single-piece electrical conductor that is directly in electrical contact with the medical device to receive the electrical signals representative of the sensed biological parameter, the elongated flex circuit extending along the entire elongated catheter shaft without interruption and without interim connection to any other electrical device and mounted to the outer surface thereof, and which terminates at the electrical catheter shaft connector located at the proximal end of the catheter shaft to thereby directly provide biological parameter electrical signals to a complementary connector that is engaged with the catheter shaft connector.

\* \* \* \* \*